(12) United States Patent
Sharma

(10) Patent No.: US 8,706,234 B2
(45) Date of Patent: Apr. 22, 2014

(54) SYSTEM AND METHOD FOR ELECTRICAL STIMULATION OF ANORECTAL STRUCTURES TO TREAT ANAL DYSFUNCTION

(76) Inventor: Virender K. Sharma, Paradise Valley, AZ (US)

(*) Notice: Subject to any disclaimer, the term of this patent is extended or adjusted under 35 U.S.C. 154(b) by 0 days.

(21) Appl. No.: 13/400,868

(22) Filed: Feb. 21, 2012

(65) Prior Publication Data

US 2013/0218229 A1 Aug. 22, 2013

(51) Int. Cl.
*A61N 1/00* (2006.01)

(52) U.S. Cl.
USPC .......................................... 607/41

(58) Field of Classification Search
USPC .......................................... 607/41
See application file for complete search history.

(56) References Cited

U.S. PATENT DOCUMENTS

| | | | |
|---|---|---|---|
| 5,702,428 A | 12/1997 | Tippey et al. | |
| 5,984,854 A | 11/1999 | Ishikawa et al. | |
| 6,243,607 B1 * | 6/2001 | Mintchev et al. | 607/40 |
| 6,449,511 B1 | 9/2002 | Mintchev et al. | |
| 6,658,297 B2 * | 12/2003 | Loeb | 607/40 |
| 6,735,474 B1 | 5/2004 | Loeb et al. | |
| 6,915,165 B2 | 7/2005 | Forsell | |
| 7,054,689 B1 | 5/2006 | Whitehurst et al. | |
| 7,765,006 B2 | 7/2010 | Martino et al. | |
| 7,765,007 B2 | 7/2010 | Martino et al. | |
| 2004/0236385 A1 | 11/2004 | Rowe et al. | |
| 2005/0192642 A1 | 9/2005 | Forsell | |
| 2006/0036293 A1 * | 2/2006 | Whitehurst et al. | 607/40 |
| 2009/0036945 A1 | 2/2009 | Chancellor et al. | |
| 2009/0222058 A1 | 9/2009 | Craggs | |
| 2009/0222060 A1 | 9/2009 | Boyd et al. | |
| 2010/0076254 A1 | 3/2010 | Jimenez et al. | |

* cited by examiner

*Primary Examiner* — Christopher D Koharski
*Assistant Examiner* — Nadia Ahmad
(74) *Attorney, Agent, or Firm* — Novel IP

(57) ABSTRACT

A system and method for treating anorectal dysfunction includes implanting, in a minimally invasive manner, an electro-medical device for stimulation of two or more separate and distinct anatomical or histological structures of the anorectal region. Electrodes operably connected to the device are positioned proximate the target anatomical or histological structures. The device provides either the same or different stimulation algorithms to each anatomical or histological structure. Smooth muscle, such as the internal anal sphincter, is provided with a continuous stimulation algorithm, while skeletal muscle, such as the external anal sphincter, is provided with an on demand stimulation algorithm. Varying stimulation algorithms applied to multiple structures results in improved anorectal function without developing muscle fatigue and tolerance.

21 Claims, 15 Drawing Sheets

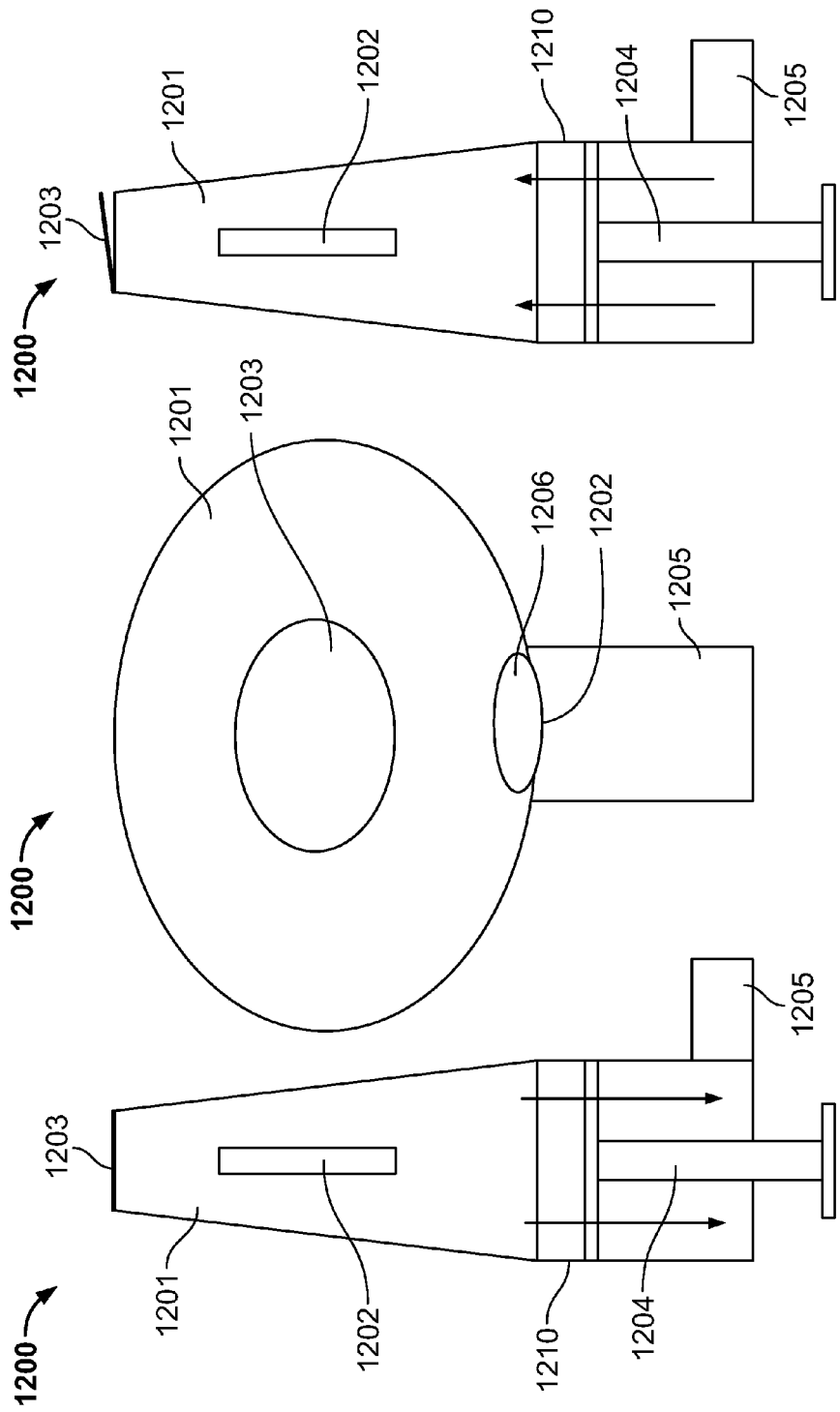

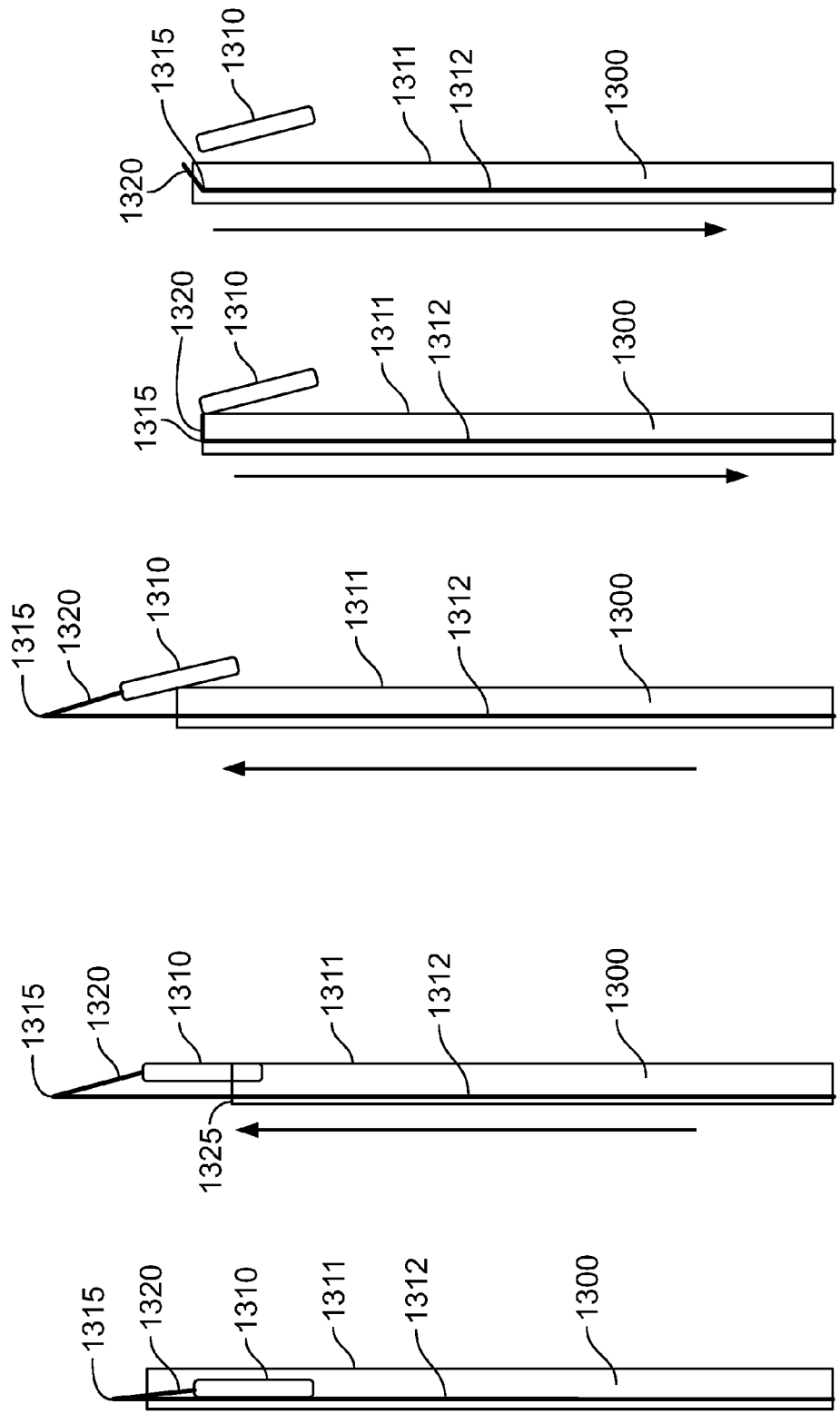

SYSTEM AND METHOD FOR ELECTRICAL STIMULATION OF ANORECTAL STRUCTURES TO TREAT ANAL DYSFUNCTION

FIELD

The present specification relates generally to a method and apparatus for electrical stimulation of the gastrointestinal tract. More particularly, the present specification relates to a method and apparatus for treating anal dysfunction by electrically stimulating the submucosa, muscularis mucosa, or muscularis propria of the rectum or anal sphincter.

BACKGROUND

Fecal incontinence refers to the involuntary loss of gas or liquid stool (minor incontinence) or the involuntary loss of solid stool (major incontinence). Surveys indicate that fecal incontinence affects between 2 and 7 percent of the general population, although the true incidence may be much higher since many people are hesitant to discuss the problem with a healthcare provider.

Minor fecal incontinence affects men and women equally, but women are almost twice as likely as men to report major incontinence. Fecal incontinence is also more common in older adults. It is particularly common in nursing home residents, with studies suggesting that almost half of all residents are incontinent. Fecal incontinence can undermine self-confidence, create anxiety, and lead to social isolation; however, fecal incontinence is a treatable condition. Treatment can lessen symptoms in most cases and can often completely cure incontinence.

Continence requires the normal function of both the lower digestive tract and the nervous system. The anal sphincters, along with the pelvic muscles that surround the end of the digestive tract, ensure controlled movement of digestive tract contents. There are many possible causes of fecal incontinence. In most cases, incontinence results from some combination of these causes.

Three types of treatment are commonly used for fecal incontinence: medical therapy, biofeedback, and surgery. Medical therapy includes medication and certain measures that can reduce the frequency of incontinence and firm up the stools, which can reduce or eliminate episodes of fecal leakage. Often, basic measures will improve minor incontinence, but more aggressive measures may be needed to control frequent or severe episodes of leakage. Bulking substances that promote bulkier stools may help control diarrhea by thickening the stools. Methylcellulose (a form of fiber) is one type of bulking substance that is commonly used. Increasing dietary fiber may also help to bulk stools. Anti-diarrheal medications such as loperamide and diphenoxylate reduce the frequency of stools and are helpful in treating fecal incontinence. Loperamide can also increase the tone (tightness) of the anal sphincter muscle. When taken before meals, anticholinergic medications (such as the prescription drug hyoscyamine), by reducing contractions in the colon, can decrease the incontinence that occurs after meals in some people.

Biofeedback is a safe and noninvasive way of retraining muscles. During biofeedback training, sensors are used to help the patient identify and contract the anal sphincter muscles which help maintain continence. This is usually done in a healthcare provider or physical therapist's office. Biofeedback can be successful, although results can be variable. The people most likely to benefit from this type of therapy are those who can contract the anal sphincter muscle and have some sensation when they need to have a bowel movement. The effects of biofeedback may begin to decline six months after the initial training and retraining may be helpful.

Sacral nerve electrical stimulation can eliminate leakage in 40 to 75 percent of people whose anal sphincter muscles are intact. An electrode is surgically inserted near a nerve in the sacrum (low back). It is not entirely clear how sacral nerve stimulation works. The treatment is invasive, requiring surgical implantation. Some patients develop complications from the surgery, including pain, device malfunction, or infection, which may require that the device be removed or replaced. At present, this treatment is generally reserved for people with an intact or repaired anal sphincter who have not shown improvement with other treatments.

Electrical stimulation of the anal sphincter involves using a mild electrical current to stimulate the anal sphincter muscles to contract, which can strengthen the muscles over time. The electrical current is applied using a small probe, which the patient inserts inside the rectum for a few minutes every day for 8 to 12 weeks. A controlled trial suggested that electrical stimulation is only a modest benefit, possibly from increasing sensation in the anal area; this treatment, however, is inexpensive, non-invasive, and has few to no side effects. It may, however, be uncomfortable for patients who understandably may not like frequently inserting the stimulator device.

Several different surgical procedures can help alleviate fecal incontinence. Surgical repair can reduce or resolve incontinence, particularly for women who develop a tear in the external anal sphincter during childbirth and in people with injury of the sphincter due to surgery or other causes. Surgery cures fecal incontinence in 80 percent of women with childbirth-related sphincter tears.

In people who have irreparable damage of the sphincters, muscles can be transferred from other areas of the body, usually the leg or buttock, and surgically placed around the anal canal. These muscles mimic the action of the damaged sphincters. Muscle transfer surgery can restore continence in up to 73 percent of people with otherwise irreparable damage. An alternative to a transferred muscle is a synthetic anal cuff that can be inflated to hold back feces and deflated to allow bowel movements. However, this type of procedure is only performed in specialized centers. Complications can occur even when these surgeries are performed by experts.

Colostomy is a surgical procedure in which the colon is surgically attached to the abdominal wall. Stool is collected in a bag that fits snugly against the skin. This eliminates leakage of stool from the rectum. Variations on the procedure may allow the person to control bowel emptying. Colostomy is usually a last resort, after other treatments have failed. It may also be considered for people with intolerable symptoms who are not candidates for any other therapy.

Prior art systems and methods for electrical stimulation address the anal sphincter, on a collective basis, and do not distinguish between internal and external anal sphincter stimulation, which can produce quite different physiological results. The internal anal sphincter is a smooth muscle which is tonically contracted, is not under voluntary control, and is innervated by the submucosal nerve plexus. The internal anal sphincter maintains the tone of the sphincter and is resistant to fatigue. On the other hand, the external anal sphincter is a skeletal muscle which is not tonically contracted, is under voluntary control, and is innervated by the sacral and pudendal nerves, providing the voluntary control to the sphincter muscle, which is extremely susceptible to fatigue. Resting pressure is provided mostly by the internal anal sphincter, whereas squeezing pressure is provided by the external sphincter.

It would therefore be advantageous to stimulate the two sphincters differentially with different stimulation algorithms or different lead configurations due to their distinct physiology and function to prevent fatigue and improve tolerance. Since sphincter control relies on multiple mechanisms, specifically with respect to energy efficiency, tolerance, and fatigue issues, it is advantageous to stimulate multiple structures with different stimulation algorithms. In order to electrically stimulate two anatomical structures, prior art systems and methods would require at least two pairs of stimulation electrodes (that is, at least two microdevices or at least four leads). Due to anatomical limitations, it may be difficult to accommodate or precisely place multiple leads into the anal sphincter. It would, however, be advantageous to put one electrode in each individual structure, thereby using less leads and/or microdevices to achieve the desired stimulation scenario.

Accordingly, there is a need for a safe and effective method of treatment that can help alleviate symptoms of anal incontinence in the long term, without the need for invasive surgery. In addition, there is not only a need for improved devices in electrical stimulation based therapies for anal incontinence, but there is also a need for a safe and minimally invasive method and system that enables easy and expeditious deployment of such devices at any desired location in the body. Most of the currently available devices are available for surgical or laparoscopic implantation and suffer from common problems of pocket infection, lead dislodgment, or fracture. Furthermore, there is also a need for a device and method for implanting microdevices within the rectum or the anal canal.

SUMMARY

In one embodiment, the present specification describes a method of treating anorectal dysfunction in a patient, comprising the following steps: providing a device comprising at least a first electrode and a second electrode operably connected to a stimulus generator; implanting said device in the anorectal tissue of the patient; positioning said first electrode in electrical communication with a first target tissue within the anorectal region of the patient; positioning said second electrode in electrical communication with a second target tissue within the anorectal region of the patient, wherein said second target tissue is distinct and different from said first target tissue; and, causing said stimulus generator to generate a first stimulation algorithm and a second stimulation algorithm, wherein said first stimulation algorithm sends a first electrical stimulation to said first target tissue via said first electrode and said second stimulation algorithm sends a second electrical stimulation to said second target tissue via said second electrode.

In one embodiment, said first target tissue and said second target tissue are chosen from any of the following: the longitudinal muscle of the rectum, the circular muscle of the rectum, the muscularis mucosa of the rectum, the submucosa of the rectum, the pudendal nerve or a branch of the pudendal nerve, a conjoined longitudinal muscle, the superficial or deep parts of the external anal sphincter, the internal anal sphincter, the muscularis mucosa of the anal canal, the subserosal plexus, the longitudinal intramuscular plexus, the circular intramuscular plexus, the periglandular plexus, the myenteric (Auerbach's) plexus, or the submucosal (Meissner's) plexus of the anorectum.

In one embodiment, said first stimulation algorithm and said second algorithm are programmable and generate pulse trains, wherein said pulse trains are variable in the number of pulses per pulse train, the shape of pulses in a pulse train, the interval between pulse train repetitions, the duration of each pulse, the timing and amplitude of pulses in each train, the desired amount of amperage or potential to be provided, and the shape of each train, wherein the shape is chosen from any one of the following: a square, rectangular, sinusoidal, or saw tooth shape.

In one embodiment, said first stimulation algorithm is the same as said second stimulation algorithm. In another embodiment, said first stimulation algorithm is different than said second stimulation algorithm.

In one embodiment, in which the first and second stimulation algorithms are the same, the same stimulation algorithm is delivered through each electrode while one electrode functions as a depolarizing electrode and the other electrode functions as a hyperpolarizing electrode. In one embodiment, when stimulation of the internal anal sphincter is desired, the electrode proximate the internal anal sphincter will be the depolarizing electrode. In one embodiment, when stimulation of the external anal sphincter is desired, the electrode proximate the external anal sphincter will be the depolarizing electrode and the alternate electrode will be the hyperpolarizing electrode.

In one embodiment, in which the first stimulation algorithm is different than the second stimulation algorithm, the first stimulation algorithm is designed to predominantly modulate the function of the internal anal sphincter, while the second stimulation algorithm is designed to predominantly modulate the function of the external anal sphincter. In one embodiment, the first stimulation algorithm is delivered continuously or at regular intervals, while the second stimulation algorithm is delivered intermittently on an as needed basis. In one embodiment, the first stimulation algorithm is programmed into the device to be automatically delivered to the patient and the second stimulation algorithm is delivered by the patient using an external input.

In one embodiment, said device further comprises at least one sensor, wherein said sensor detects at least one parameter, further wherein data obtained by said sensor is used to modify said first stimulation algorithm and/or said second stimulation algorithm. In one embodiment, said sensor comprises a pressure sensor, an electrical activity sensor, an impedance sensor, an accelerometer, or an inclinometer. In another embodiment, the sensor comprises an internal pressure sensor, wherein the patient initiates an anal squeeze, further wherein said squeeze is sensed by said internal pressure sensor, resulting in said device delivering a stimulation specific for the external anal sphincter to raise the external anal sphincter tone.

In one embodiment, said device further comprises an external controller designed to be operated by said patient, wherein the patient is capable of modifying and activating said first stimulation algorithm and/or said second algorithm.

In one embodiment, the device is programmed based on the patient's clinical symptoms, rectal manometry data or other clinical or investigational data to program a patient specific stimulation algorithm.

In one embodiment, the specification describes a device for treating anorectal dysfunction in a patient, comprising: a microcontroller, comprising a transceiver for receiving and transmitting data and/or power from outside the patient's body through inductive, radiofrequency (RF), electrical, magnetic, optical or other electromagnetic coupling; an integrated circuit (IC) chip for decoding and storing a plurality of stimulation parameters and generating a plurality of stimulation pulses; and, a programmable memory for storing sets of data, stimulation, and control parameters; a stimulus generator; a power source; and, at least two electrodes for implantation into and stimulation of anorectal tissue.

In one embodiment, the device for treating anorectal dysfunction in a patient further comprises at least one sensor as described above. In one embodiment, the device further comprises at least one anchor used to anchor the device in the rectum or the anal canal. In one embodiment, the device further comprises an external controller designed to be operated by said patient as described above.

In one embodiment, the present specification describes a catheter device for implanting a microdevice in the anorectum, comprising: an elongate sheath having a proximal open end and a distal open end; an elongate pusher slidably movable within said sheath, comprising: a proximal end and a distal end; a sharp bend proximate said distal end; and, an attachment point at its distal end, distal to said sharp bend, for the attachment of said microdevice.

In one embodiment, the present specification describes a device for assisting in the implantation of a microdevice in the anorectum, comprising: a conical, distal portion comprising: a distal end and a proximal end, wherein said distal end has a smaller diameter than said proximal end; a rectangular slot for capturing a portion of anorectal tissue; an opening at said distal end; and, a moveable valve covering said opening at said distal end; a cylindrical, proximal portion, comprising: a distal end and a proximal end, wherein said distal end is attached to and in open communication with, said proximal end of said distal portion; and, a handle; a means for creating a vacuum within said device, said vacuum sucking a portion of anorectal tissue in through the slot and into the distal portion; and, a channel extending through said proximal portion and into said distal portion for the passage of a catheter or needle. In one embodiment, the means for creating a vacuum comprises a plunger inserted into the proximal end of, and slidably movable within, the proximal portion of the insertion device. In another embodiment, the means for creating a vacuum comprises suction applied to the proximal end of the proximal portion of the insertion device.

In one embodiment, the present specification describes a method for implanting a microdevice in the anorectal region of a patient, comprising the steps of: providing an insertion device, said insertion device comprising: a conical, distal portion comprising: a distal end and a proximal end, wherein said distal end has a smaller diameter than said proximal end; a rectangular slot for capturing a portion of anorectal tissue; an opening at said distal end; and, a moveable valve covering said opening at said distal end; a cylindrical, proximal portion, comprising: a distal end and a proximal end, wherein said distal end is attached to and in open communication with, said proximal end of said distal portion; and, a handle; a means for creating a vacuum within said device, said vacuum sucking a portion of anorectal tissue in through the slot and into the distal portion; and, a channel extending through said proximal portion and into said distal portion for the passage of a catheter or needle; providing a catheter, said catheter comprising: an elongate sheath having a proximal open end and a distal open end; an elongate pusher slidably movable within said sheath, comprising: a proximal end and a distal end; a sharp bend proximate said distal end; and, an attachment point at its distal end, distal to said sharp bend, for the attachment of said microdevice; inserting said insertion device into a patient's rectum; using said vacuum creating means to create a vacuum within said insertion device and suck in a portion of anorectal tissue into said insertion device; inserting said catheter into said channel of said insertion device; extending said pusher with an attached microdevice past the distal open end of said sheath, causing said sharp bend to partially expand; pulling said pusher back into said sheath, causing said microdevice to become engaged with said anorectal tissue; fully retracting said pusher into said sheath, causing said microdevice to detach from said pusher and remain in said anorectal tissue; disengaging said vacuuming means to release vacuum and release said portion of anorectal tissue; and, removing said insertion device from the patient's rectum.

In one embodiment, the present specification describes a system for treating anorectal dysfunction in a patient, comprising: at least one electro-medical device, said electro-medical device comprising a microcontroller, said microcontroller comprising a transceiver for receiving and transmitting data and/or power from outside the patient's body through inductive, radiofrequency (RF), electrical, magnetic, optical or other electromagnetic coupling; an integrated circuit (IC) chip for decoding and storing a plurality of stimulation parameters and generating a plurality of stimulation pulses; and, a programmable memory for storing sets of data, stimulation, and control parameters; a stimulus generator; a power source; and, at least two electrodes for implantation into and stimulation of anorectal tissue; a catheter for implanting said electro-medical device, said catheter comprising: an elongate sheath having a proximal open end and a distal open end; an elongate pusher slidably movable within said sheath, comprising: a proximal end and a distal end; a sharp bend proximate said distal end; and, an attachment point at its distal end, distal to said sharp bend, for the attachment of said microdevice; and, an insertion device for assisting in said implantation, said insertion device comprising: a conical, distal portion comprising: a distal end and a proximal end, wherein said distal end has a smaller diameter than said proximal end; a rectangular slot for capturing a portion of anorectal tissue; an opening at said distal end; and, a moveable valve covering said opening at said distal end; a cylindrical, proximal portion, comprising: a distal end and a proximal end, wherein said distal end is attached to and in open communication with, said proximal end of said distal portion; and, a handle; a means for creating a vacuum within said device, said vacuum sucking a portion of anorectal tissue in through the slot and into the distal portion; and, a channel extending through said proximal portion and into said distal portion for the passage of a catheter or needle.

In one embodiment, the present specification is directed toward a method of modulating the function of an internal anal sphincter in a patient, comprising the following steps: providing a device comprising at least a first electrode and a second electrode operably connected to a stimulus generator; implanting said device in the anorectal tissue of the patient; positioning said first electrode in electrical communication with a first target tissue within the anorectal region of the patient; positioning said second electrode in electrical communication with a second target tissue within the anorectal region of the patient, wherein said second target tissue is the same as or distinct and different from said first target tissue; and, causing said stimulus generator to generate a stimulation, wherein said stimulation is adapted to modulate the function of an internal anal sphincter that lasts beyond the cessation of such stimulation. In one embodiment, the modulation of a function of the internal anal sphincter lasts for at least 5 minutes after the cessation of the stimulation.

In one embodiment, the present specification is directed toward a method of modulating the function of an internal anal sphincter in a patient, comprising the following steps: providing a device comprising at least a first electrode and a second electrode operably connected to a stimulus generator; implanting said device in the anorectal tissue of the patient;

positioning said first electrode in electrical communication with a first target tissue within the anorectal region of the patient; positioning said second electrode in electrical communication with a second target tissue within the anorectal region of the patient, wherein said second target tissue is the same as or distinct and different from said first target tissue; and, causing said stimulus generator to generate a stimulation, wherein said stimulation is adapted to modulate the function of an internal anal sphincter and wherein such modulation of the internal anal sphincter function is further modulated by rectal distension. In one embodiment, the additional modulation of the internal anal sphincter function by rectal distension results in an increase or a decrease by at least 10% of the initial modulation of said function due to the stimulation.

In another embodiment, the present specification discloses a method of treating anorectal dysfunction in a patient, comprising the following steps: implanting a device comprising at least a first electrode and a second electrode operably connected to an electrical stimulus generator in anorectal tissue of the patient, wherein said anorectal tissue comprises a first target tissue and a second target tissue and wherein said first target tissue is distinct and different from said second target tissue; causing said stimulus generator to deliver a first electrical pulse via said first electrode to the first target tissue; and causing said stimulus generator to deliver a second electrical pulse via said second electrode to the second target tissue. Optionally, the first electrode physically contacts the first target tissue and wherein the second electrode physically contacts the second target tissue.

Optionally, the first target tissue and said second target tissue are at least one of the following: the longitudinal muscle of the rectum, the circular muscle of the rectum, the muscularis mucosa of the rectum, the submucosa of the rectum, the pudendal nerve or a branch of the pudendal nerve, a conjoined longitudinal muscle, the superficial or deep parts of the external anal sphincter, the internal anal sphincter, the muscularis mucosa of the anal canal, the subserosal plexus, the longitudinal intramuscular plexus, the circular intramuscular plexus, the periglandular plexus, the myenteric (Auerbach's) plexus, or the submucosal (Meissner's) plexus of the anorectum. Optionally, the stimulus generator is capable of generating pulse trains and wherein at least one of the following parameters is programmable: numbers of pulses per pulse train, intervals between pulse trains, durations of each pulse, timings and amplitudes of pulses in a pulse train, desired amounts of amperage or potential in a pulse, or shapes of pulses in pulse trains, wherein the shape is chosen from any one of the following: a square, rectangular, sinusoidal, or saw tooth shape.

Optionally, the stimulus generator generates the first electrical pulse pursuant to a first stimulation algorithm and said stimulus generator generates the second electrical pulse pursuant to a second stimulation algorithm. Optionally, the first electrode functions as a depolarizing electrode and said second electrode functions as a hyperpolarizing electrode. Optionally, the depolarizing electrode is positioned proximate the patient's internal anal sphincter for stimulation of said internal anal sphincter.

Optionally, the depolarizing electrode is positioned proximate the patient's external anal sphincter for stimulation of said external anal sphincter. Optionally, the first stimulation algorithm is different than said second stimulation algorithm. Optionally, the first stimulation algorithm is configured to modulate a function of the patient's internal anal sphincter and said second stimulation algorithm is configured to modulate a function of the patient's external anal sphincter.

Optionally, the first stimulation algorithm causes the first electrical pulse to be delivered continuously or at regular intervals and said second stimulation algorithm causes the second electrical pulse to be delivered at irregular intervals or on demand. Optionally, the first stimulation algorithm is programmed into the device such that the first electrical pulse is delivered without patient intervention and said second electrical pulse is manually delivered by the patient via an external input.

Optionally, the first stimulation algorithm is programmed based on patient's clinical symptoms or rectal manometry data and stored in a memory in said device. Optionally, the device further comprises at least one sensor, wherein said sensor detects at least one parameter, and wherein data obtained by said sensor is used to modify said first stimulation algorithm and/or said second stimulation algorithm.

Optionally, the sensor comprises at least one of a pressure sensor, an electrical activity sensor, an impedance sensor, an accelerometer, or an inclinometer. Optionally, the sensor comprises an internal pressure sensor configured such that, when the patient initiates an anal squeeze, said squeeze is sensed by said internal pressure sensor and causes said device to deliver an electrical pulse to the patient's external anal sphincter to raise the external anal sphincter tone. Optionally, the device further comprises an external controller configured to be operated by said patient and wherein the external controller is adapted to modify or activate at least one of said first stimulation algorithm or said second stimulation algorithm.

In another embodiment, the present specification discloses a method of modulating a function of an internal anal sphincter in a patient, comprising the following steps: implanting a stimulus generator, wherein said stimulus generator is operably connected to a first electrode and a second electrode; implanting said first electrode within a first target tissue, wherein said first target tissue is part of the patient's anorectal region; implanting said second electrode within a second target tissue, wherein said second target tissue is part of the patient's anorectal region; and causing said stimulus generator to generate a stimulation, wherein said stimulation is adapted to modulate the function of the internal anal sphincter.

Optionally, the modulation is adapted to last beyond a cessation of such stimulation. The second target tissue is the same as, or distinct and different from, the first target tissue. The modulation lasts for at least 5 minutes after the cessation of the stimulation. The modulation of the internal anal sphincter function is further modulated by rectal distension. The additional modulation of the internal anal sphincter function by rectal distension results in an increase or a decrease by at least 10% of the modulation of said function due to the stimulation.

The aforementioned and other embodiments of the present specification shall be described in greater depth in the drawings and detailed description provided below.

BRIEF DESCRIPTION OF THE DRAWINGS

These and other objects and advantages of the present specification will become more fully apparent from the following detailed description when read in conjunction with the accompanying drawings with like reference numerals indicating corresponding parts through-out, wherein:

FIG. 12A is an illustration of one embodiment of an exemplary insertion device, depicting the step of pulling the plunger of the insertion device downward to create a vacuum thereby suctioning in a portion of anorectal tissue;

FIG. 12B is a top-down view illustration of the same embodiment of an exemplary insertion device of FIG. 12A, depicting a portion of anorectal tissue suctioned into the device;

FIG. 12C is an illustration of the same embodiment of an exemplary insertion device of FIG. 12A, depicting the step of pushing the plunger of the insertion device upward to release anorectal tissue;

FIG. 13A is an illustration of one embodiment of an exemplary configuration of an implantation catheter with a pusher and attached microdevice arranged predominantly parallel to each other within said catheter;

FIG. 13B is an illustration of the same embodiment of an exemplary configuration of an implantation catheter of FIG. 13A, depicting the microdevice being pushed out of said catheter using the pusher;

FIG. 13C is an illustration of the same embodiment of an exemplary configuration of an implantation catheter of FIG. 13A, depicting the microdevice fully pushed out of said catheter;

FIG. 13D is an illustration of the same embodiment of an exemplary configuration of an implantation catheter of FIG. 13A, depicting the pusher being pulled back into said catheter;

FIG. 13E is an illustration of the same embodiment of an exemplary configuration of an implantation catheter of FIG. 13A, depicting the pusher pulled back completely into said catheter, thereby disconnecting from the microdevice that is implanted in a tissue site;

DETAILED DESCRIPTION

Figure 1:
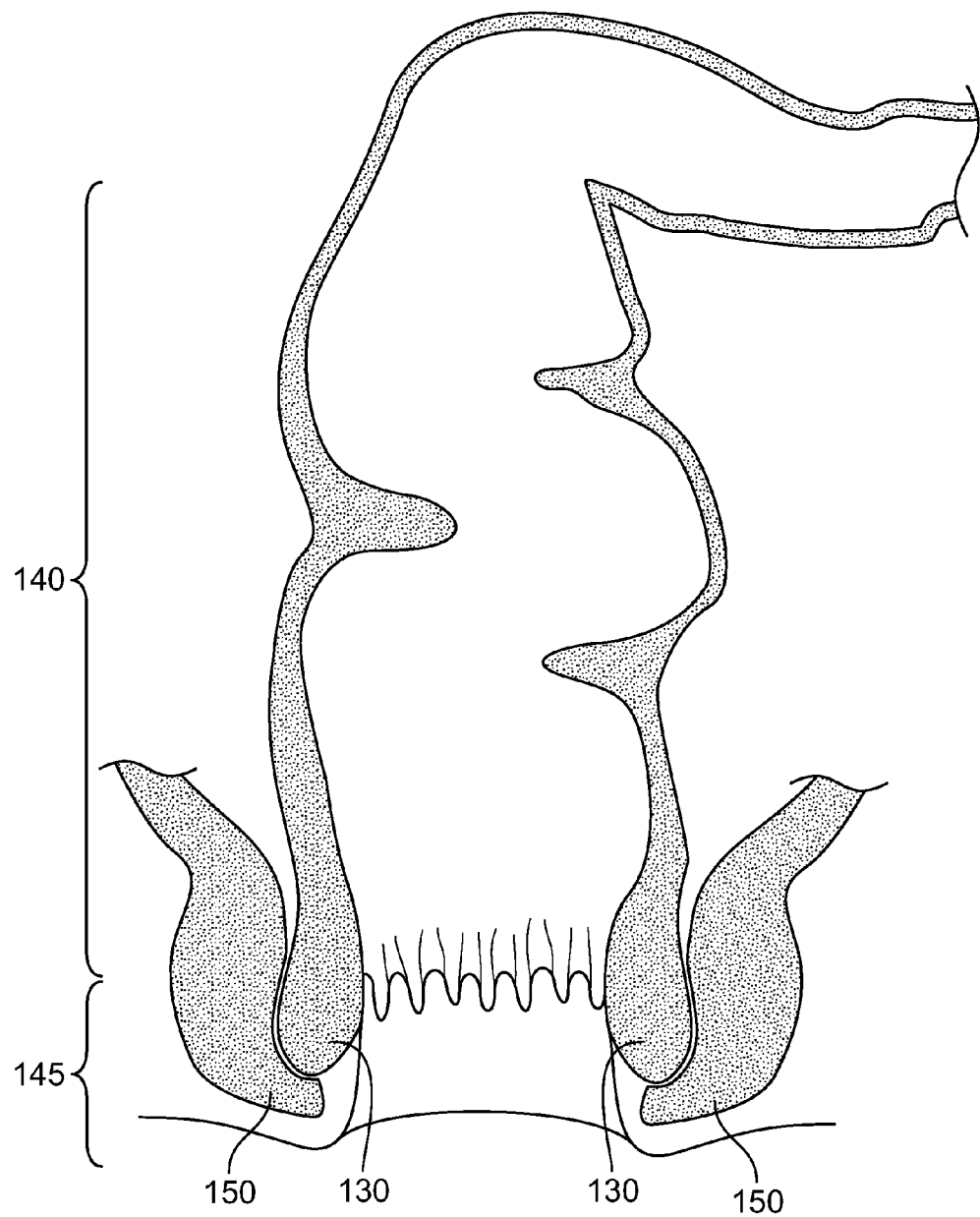
FIG. 1 is a cross sectional illustration of the rectum and anal canal.

The present specification is directed toward a programmable, implantable electro-medical device for the treatment of various anorectal neuromuscular disorders, including fecal incontinence and constipation. The electro-medical device of the present specification employs implantable microstimulators or macrostimulators that are implanted with minimal invasiveness in the anorectal region. In one embodiment, each microstimulator includes at least two electrodes used to deliver electrical stimulation to at least two separate target tissues. In one embodiment, the electro-medical device comprises a common anode or cathode in the middle and two separate electrodes, each with polarity opposite to the center electrode, at each end. In another embodiment, the device has only two electrodes, wherein the stimulating electrode is selected based on the desired region to be stimulated. In various embodiments, the electro-medical device is implanted into the mucosa, submucosa, or muscularis propria of the anorectal region. Preferably, the electro-medical device is implanted into the rectal submucosa. The rectal submucosa is a low impedance layer and is easily accessible, with implantation involving minimal risk and invasiveness. After implantation of the electro-medical device, the electrodes are endoscopically or surgically routed to each specific target tissue. In one embodiment, the electrodes are designed utilizing technology such as shape memory to allow for appropriate configurations. Differential length, shape or configuration of the electrodes will make them better suited to be proximate to the desired target tissue. A first electrode is implanted within or proximate a first target tissue and a second electrode is implanted within or proximate a second target tissue. In one embodiment, the target tissues comprise muscles and nerves in the anorectal region. In various embodiments, the target tissues comprise the longitudinal muscle of the rectum, the circular muscle of the rectum, the muscularis mucosa of the rectum, the submucosa of the rectum, the pudendal nerve or a branch of the pudendal nerve, a conjoined longitudinal muscle, the superficial or deep parts of the external anal sphincter, the internal anal sphincter, the muscularis mucosa of the anal canal, the subserosal plexus, the longitudinal intramuscular plexus, the circular intramuscular plexus, the periglandular plexus, the myenteric (Auerbach's) plexus, or the submucosal (Meissner's) plexus of the anorectum. The subcutaneous portion of the external anal sphincter lies proximate the skin and has nerve innervation overlapping with the overlying skin. Hence, it is desirable that stimulation of the subcutaneous part of the external anal sphincter is minimized or avoided to minimize sensation associated with stimulation.

The present specification is also directed toward a system and method of stimulating two separate anorectal tissues for the treatment of various anorectal neuromuscular disorders, including fecal incontinence and constipation. In various embodiments, the two target tissues are selectively stimulated simultaneously or at separate times using the same or different stimulation algorithms.

For example, in one embodiment, a first electrode is implanted in the internal anal sphincter and a second electrode is implanted in the external anal sphincter. The internal anal sphincter is provided with a first level of stimulation which is applied continuously. Meanwhile, the external anal sphincter is provided with a second level of stimulation which is applied on demand. Stimulating multiple target tissues with the same or different stimulation algorithms improves anorectal function and increases energy efficiency while avoiding fatigue and tolerance issues encountered in the prior art. Additionally, fewer devices and electrodes are required as separate target structures can receive different stimulation via different algorithms rather than from different electrodes and devices. For example, a short duration (200 μsec), high frequency pulse (20 Hz) pulse may be better suited to stimulate the internal anal sphincter to increase tone, while a long duration (300 msec), low frequency (5 cps) pulse may be better suited to stimulate the external anal sphincter. Hence, providing these different pulses through the same electrodes at different times could achieve a desired clinical effect of maintaining continence.

The present specification is also directed toward a catheter for implantation of the electro-medical device. In one embodiment, the catheter comprises a sheath and a pusher to which is attached the electro-medical device. The pusher has a sharp bend proximate its distal end. The pusher is extended past an opening at the distal end of the sheath, allowing the sharp bend to partially expand and exposing the electro-medical device. The pusher is then retracted back into the sheath, pushing the electro-medical device into the anorectal tissue. As the pusher is fully retracted into the sheath, the electro-medical device disengages from its distal end.

The present specification is also directed toward an insertion device for assisting in the delivery of the catheter and implantation of the electro-medical device. In one embodiment, the insertion device comprises a conical, distal portion and a cylindrical, proximal portion. In one embodiment, a moveable valve covers an opening at the distal end of the distal portion. The distal portion includes a slot for capturing a portion of anorectal tissue. In one embodiment, a plunger is slidably movable within the proximal portion and is used to create a vacuum and suck a portion of anorectal tissue in through the slot and into the distal portion. Alternatively, in another embodiment, external suction using a pump is applied to engage the anorectal tissue. The catheter, as described above, is then used to implant the electro-medical device.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 2:
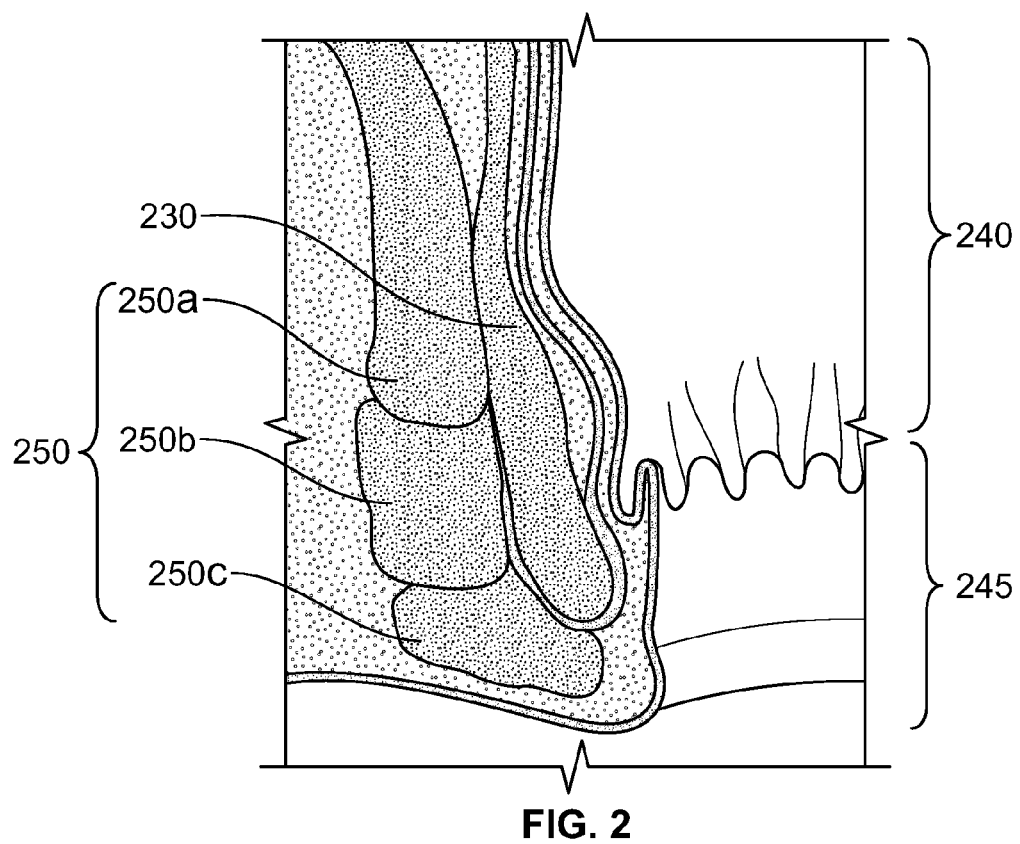
FIG. 2 is a cross sectional illustration of the musculature of one side of the lower rectum and anal canal.
Figure 3:
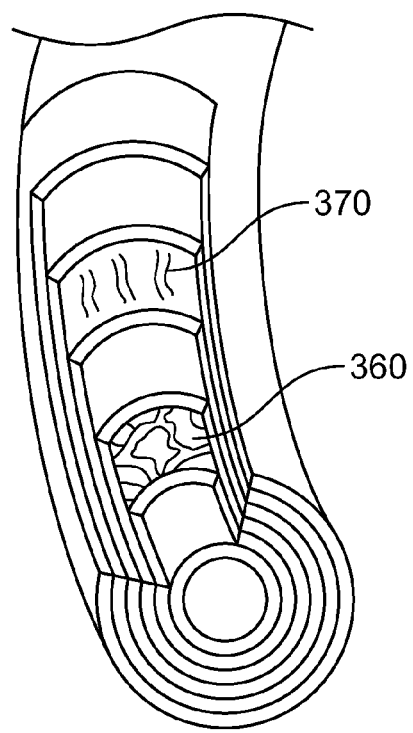
FIG. 3 is a cut away illustration of the lower colon, depicting nerve plexuses in the wall of the rectum and anal canal.

Persons of ordinary skill in the art would appreciate that normal anorectal function, including continence, is a complex mechanism that requires both involuntary (subconscious) and voluntary (conscious) control of the anal sphincter musculature. FIG. 1 is a cross sectional illustration of the rectum 140 and anal canal 145. FIG. 2 is a cross sectional illustration of the musculature of one side of the lower rectum 240 and anal canal 245. FIG. 3 is a cut away illustration of the lower colon, depicting nerve plexuses 360, 370 in the wall of the rectum and anal canal. Referring now to FIGS. 1 through 3 simultaneously, the internal anal sphincter 130, 230 is a smooth muscle under involuntary control, is innervated by the submucosal (Meissner's) nerve plexus 360 and myenteric (Auerbach's) nerve plexus 370 in the intestinal wall, and is responsible for the resting tone of the sphincter. The external anal sphincter 150, 250 is a skeletal muscle under voluntary control, is innervated by the perineal branch of the fourth sacral nerve and the inferior rectal nerve, and is responsible for the squeeze pressure and voluntary tone of the sphincter. As can be seen in FIG. 2, the external anal sphincter is further divided into deep 250a, superficial 250b, and subcutaneous 250c components. Due to its smooth muscle composition, the internal anal sphincter 130, 230 is less prone to fatigue and can generate low levels of pressures for prolonged durations. On the other hand, the external anal sphincter 150, 250 is a skeletal muscle and hence can generate high voluntary pressures for short durations. However, it easily fatigues within minutes and cannot maintain a sustained high tone.

The electro-stimulation treatment methods of the present specification appreciate that the internal and external anal sphincter muscles are histologically and functionally distinct and require differential stimulation for optimal function. The internal anal sphincter requires prolonged stimulation to maintain the basal tone and prevent seepage of stool and mucus from the anus. Since normal defecation can be achieved even in the presence of continuous internal sphincter stimulation, sensing for defecation and inhibition of internal anal sphincter stimulation is unnecessary. The external anal sphincter requires short bursts of stimulation to generate squeeze pressure to overcome the urge to defecate. The present specification addresses the issue that continuous or prolonged stimulation of the external anal sphincter will lead to fatigue and pain by providing different stimulation algorithms to each target tissue.

In one embodiment, the same stimulation algorithm is delivered through each electrode while one electrode functions as a depolarizing electrode and the other electrode functions as a hyperpolarizing electrode. When stimulation of the internal anal sphincter is desired, the electrode proximate the internal anal sphincter will be the depolarizing electrode. When stimulation of the external anal sphincter is desired, the electrode proximate the external anal sphincter will be the depolarizing electrode and the alternate electrode will be the hyperpolarizing electrode.

In one embodiment, in which one stimulation algorithm is different than the other stimulation algorithm, the first stimulation algorithm is designed to predominantly modulate the function of the internal anal sphincter, while the second stimulation algorithm is designed to predominantly modulate the function of the external anal sphincter. In one embodiment, the first stimulation algorithm is delivered continuously or at regular intervals, while the second stimulation algorithm is delivered intermittently on an as needed basis. In one embodiment, the first stimulation algorithm is programmed into the device to be automatically delivered to the patient and the second stimulation algorithm is delivered by the patient using an external input.

In one embodiment, two or more stimulation algorithms can serve different functions. For example, a stimulating algorithm used to raise muscle tone can be combined with a blocking pulse algorithm to block the sensation arising from the patient's rectum or anal canal, to block the patient's urge to defecate.

Submucosal space is a low impedance space comprising loose connective tissues and the submucosal (Meissner's) nerve plexus 360. Therefore, in accordance with an aspect of the present specification, submucosal space is identified to be easily accessible for safe implantation of a microdevice and also for stimulation with more energy efficient algorithms.

Figure 4:
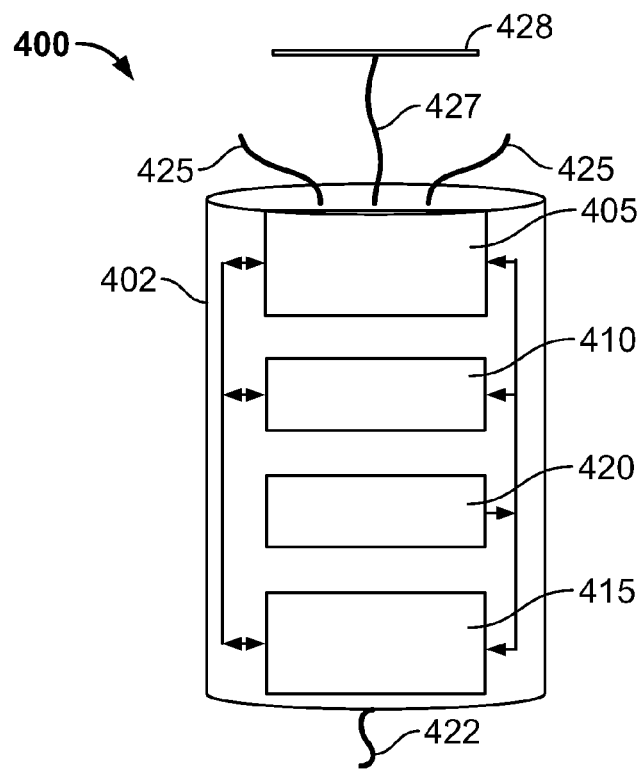
FIG. 4 is a schematic illustration of an exemplary programmable implantable electro-medical microdevice, in accordance with one embodiment of the present specification.

FIG. 4 is a schematic illustration of an exemplary programmable, implantable electro-medical microdevice 400, in accordance with one embodiment of the present invention. The microdevice 400 comprises a stimulator or waveform generator 405, a microcontroller 410, an optional sensor module 415 and a power source 420, all integrated into a single unit for easy and quick deployment within the anorectal region of a patient. The stimulator 405, microcontroller 410 and sensor module 415 are capable of communicating with each other using wired or wireless communication.

Referring to FIG. 4, the microdevice 400 comprises an outer shell 402 of a biocompatible, hermetically sealed material such as glass, ceramic, polymers, titanium, or any other suitable material evident to persons of ordinary skill in the art. In one embodiment, the microcontroller 410 comprises: a transceiver for receiving and transmitting data and/or power from outside the patient's body through inductive, radiofrequency (RF), electrical, magnetic, optical or other electromagnetic coupling; an integrated circuit (IC) chip for decoding and storing a plurality of stimulation parameters and generating a plurality of stimulation pulses; and, a programmable memory for storing sets of data, stimulation, and control parameters. Programmable memory allows for stimulation and control parameters to be adjusted for each individual patient by means of inductive, radiofrequency (RF), or other electromagnetic coupling, to settings that are safe, efficacious, and minimize discomfort.

The stimulator or waveform generator 405 is an electrophysiological stimulator capable of generating a plurality of desired electrical pulses for stimulating appropriate nerves and/or muscles in the anorectal region of the patient. The stimulator 405 generates a plurality of stimulus pulse trains as directed by the microcontroller 410. In one embodiment, the pulse trains are programmable and their characteristics can vary in the following ways: the number of pulses in a pulse train; the shape of pulses in a pulse train; the interval between pulse train repetitions; the duration of each pulse; the timing and amplitude of pulses in trains; and, the desired amount of amperage or potential to be provided, depending upon the condition and need of the patient. Further, the electrical stimulus may have any shape necessary to produce the desired result, including a square, rectangular, sinusoidal, or saw tooth shape. In one embodiment, the desired stimulus pulse is delivered through a plurality of stimulation electrodes 425.

In one embodiment, the stimulus is triggered by the patient using a transmitter external to the patient's body, similar to a remote transmitter for a cardiac pacemaker as known to persons of ordinary skill in the art. In one embodiment, the transmitter is an external handheld device.

In one embodiment, the power source includes an external power source coupled to the microdevice 400 via a suitable means, such as RF link. In another embodiment, the power source includes a self-contained power source 420 utilizing any suitable means of generation or storage of energy such as a primary battery, a replenishable or rechargeable battery such as a lithium ion battery, an electrolytic capacitor, etc.

In one embodiment, the optional sensor module 415 uses a plurality of sensing electrodes 422 to detect a plurality of physiological parameters such as pressure, electrical activity, and impedance. In another embodiment, the optional sensor module 415 includes an accelerometer to detect changes in patient position. In one embodiment, the optional sensor module 415 includes an inclinometer. The information gathered by the optional sensor module 415 is used to trigger stimulation and/or to modify on and off cycles of stimulation.

In another embodiment the patient can perform a maneuver that is sensed by an internal sensor to deliver a specific stimulation. For example, the patient can initiate a squeeze that is sensed by an internal pressure sensor to deliver a stimulation specific for the external anal sphincter to raise the external anal sphincter tone.

In one embodiment, the microdevice 400 also includes an anchor 428 that enables anchoring of the microdevice 400 to appropriate sites in the anorectal region of the patient. The anchoring element 428 is fixed to the microdevice 400 through an attachment 427. In one embodiment, the attachment 427 contracts after deployment, pulling the microdevice 400 deeper into the particular site or snug with the wall, thereby providing better retention.

In one embodiment, the plurality of stimulating electrodes 425 and sensing electrodes 422 are made up of a conducting ceramic, conducting polymer, and/or a noble or refractory metal. Persons of ordinary skill in the art should appreciate that, depending on the application, site, or desired physiological stimulus, an electrode can be used both as a sensing as well as a stimulation electrode. In various embodiments, the sensing electrode 422 and anchor 428 or the stimulating electrode 425 and anchor 428 may be the same element. In still other embodiments, the same element may be used as stimulating electrode 425, sensing electrode 422 and anchor 428.

In accordance with one embodiment of the method of treatment of the present specification, the stimulation pulses are delivered along the lines of the following parameters:
Frequency=1 cpm-100 Hz;
Amplitude=1 uAmp-100 mAmp;
Pulse width=1 msec-1 sec; and,
Duty cycle<100%

According to one embodiment, the treatment regimen comprises treating continuously with an on cycle of stimulation and an off cycle of stimulation. For example, the muscularis mucosa of the anal canal and the internal anal sphincter is treated continuously with an on cycle of stimulation and an off cycle of stimulation. In one embodiment, the on cycle of stimulation is 1 msec-23 hrs and the off cycle of stimulation is 1 msec-23 hrs.

Figure 5:
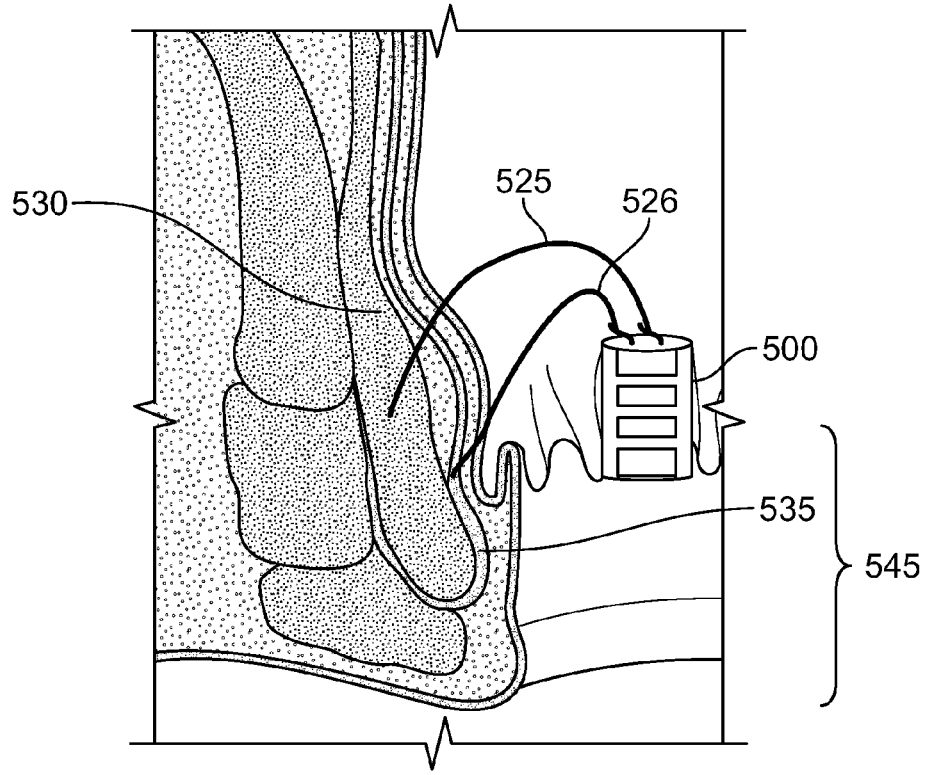
FIG. 5 is an illustration of one embodiment of an exemplary electrode set of a microdevice implanted in the internal anal sphincter and muscularis mucosa of the anal canal.

FIG. 5 is an illustration of one embodiment of an exemplary electrode set 525, 526 of a microdevice 500 implanted in the internal anal sphincter 530 and muscularis mucosa 535 of the anal canal. The microdevice 500 is implanted such that a first electrode 525 is proximate the internal anal sphincter 530 and a second electrode 526 is proximate the muscularis mucosa 535 of the anal canal 545.

Figure 6:
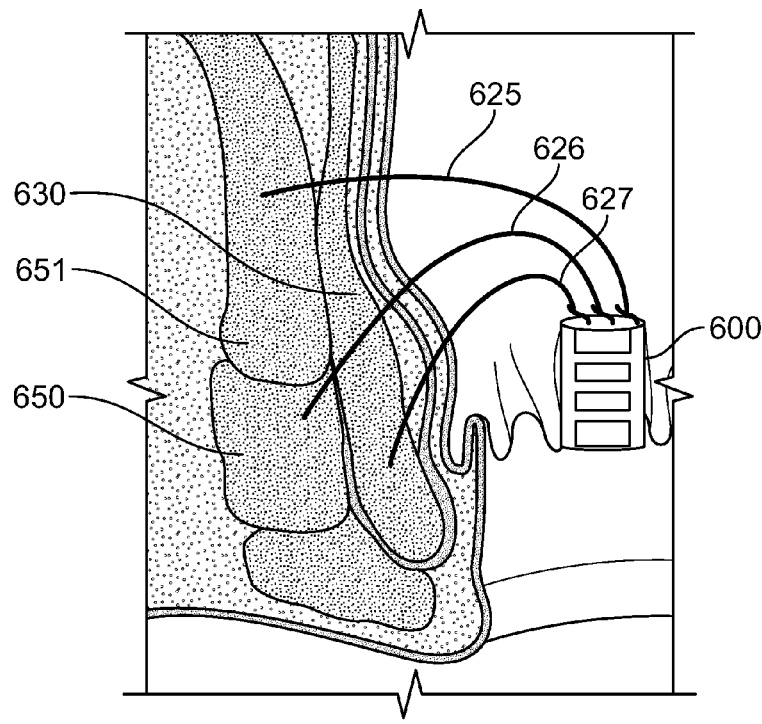
FIG. 6 is an illustration of one embodiment of an exemplary electrode set of a microdevice implanted in the superficial and deep part of the external anal sphincter and in the internal anal sphincter.

FIG. 6 is an illustration of one embodiment of an exemplary electrode set 625, 626 627 of a microdevice 600 implanted in the superficial 650 and deep 651 parts of the external anal sphincter and the internal anal sphincter muscle 630. The microdevice 600 is implanted such that two first electrodes 626, 625 are proximate the superficial part 650 and the deep part 651 of the external anal sphincter respectively, while a third electrode 627 is proximate the internal anal sphincter 630.

Figure 7:
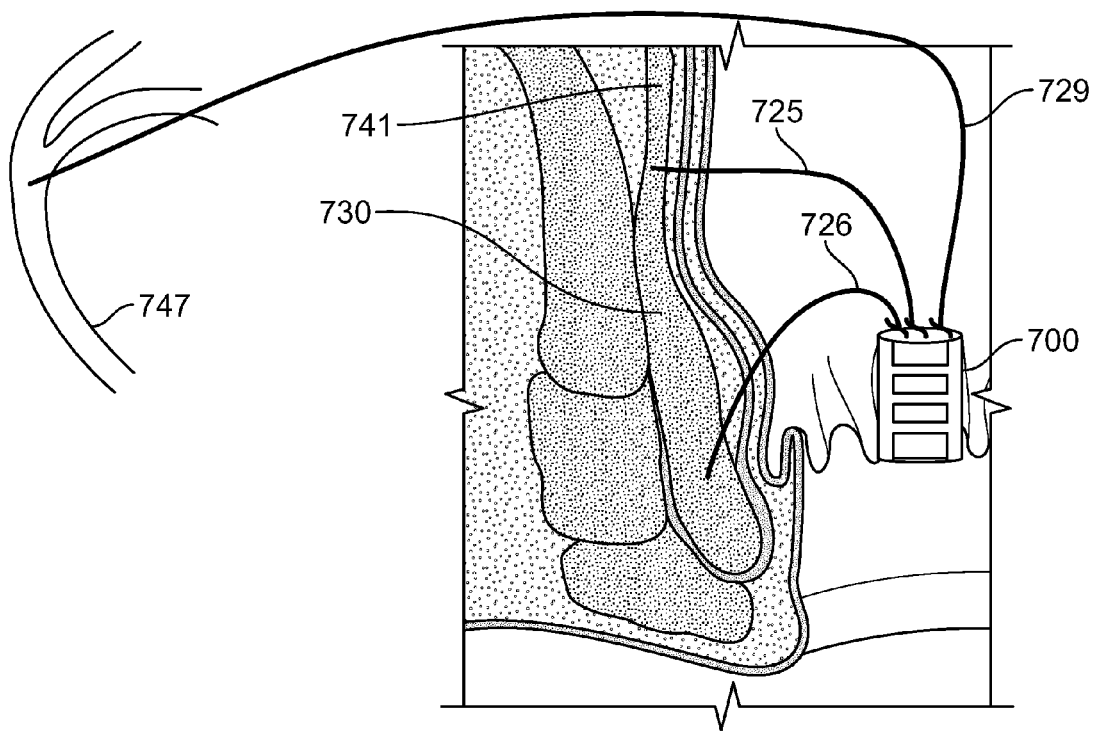
FIG. 7 is an illustration of one embodiment of an exemplary electrode set of a microdevice implanted in the circular muscle of the rectum, the internal anal sphincter, and proximate a branch of the pudendal nerve.

FIG. 7 is an illustration of one embodiment of an exemplary electrode set 725, 726, 729 of a microdevice 700 implanted in the circular muscle of the rectum 741, the internal anal sphincter muscle 730, and proximate a branch of the pudendal nerve 747. The microdevice 700 is implanted such that a first electrode 725 is proximate the circular muscle layer of the rectum 741 while a second electrode 726 is proximate the internal anal sphincter muscle 730. A third electrode 729 is placed proximate a branch of the pudendal nerve 747.

Figure 8:
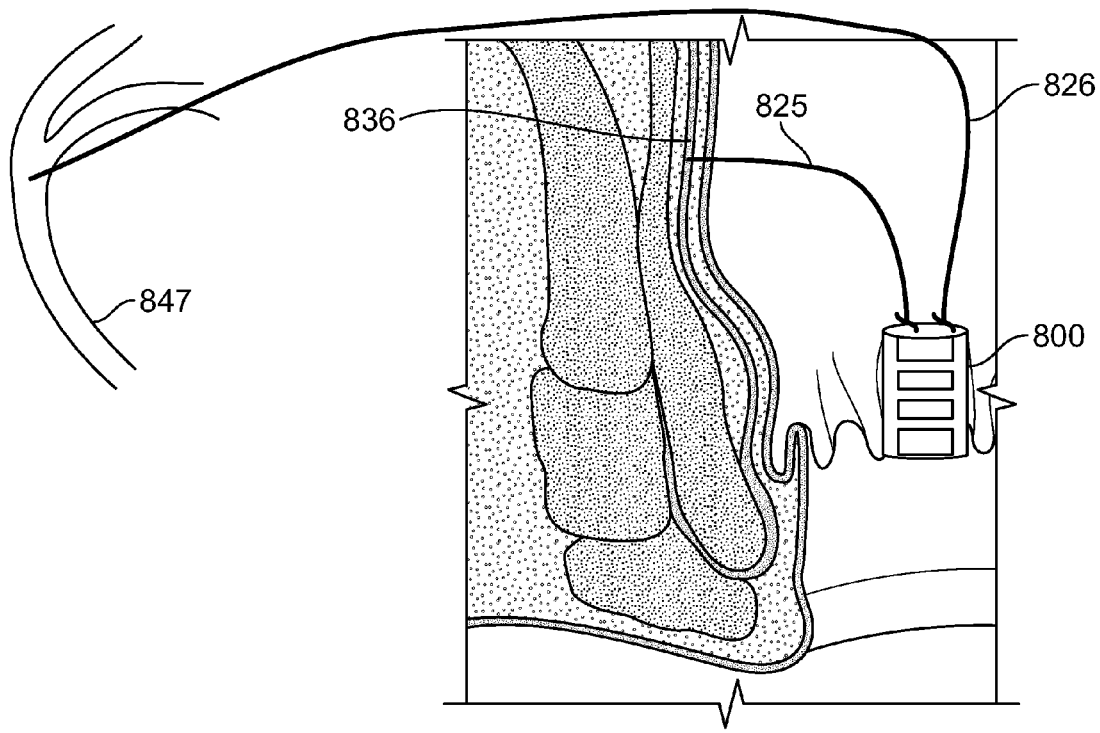
FIG. 8 is an illustration of one embodiment of an exemplary electrode set of a microdevice implanted in the submucosa of the rectum and in a branch of the pudendal nerve.

FIG. 8 is an illustration of one embodiment of an exemplary electrode set 825, 826 of a microdevice 800 implanted in the submucosa of the rectum 836 and in a branch of the pudendal nerve 847. The microdevice 800 is implanted such that a first electrode 825 is proximate the submucosa of the rectum 836 while a second electrode 826 is proximate a branch of the pudendal nerve 847.

Figure 9:
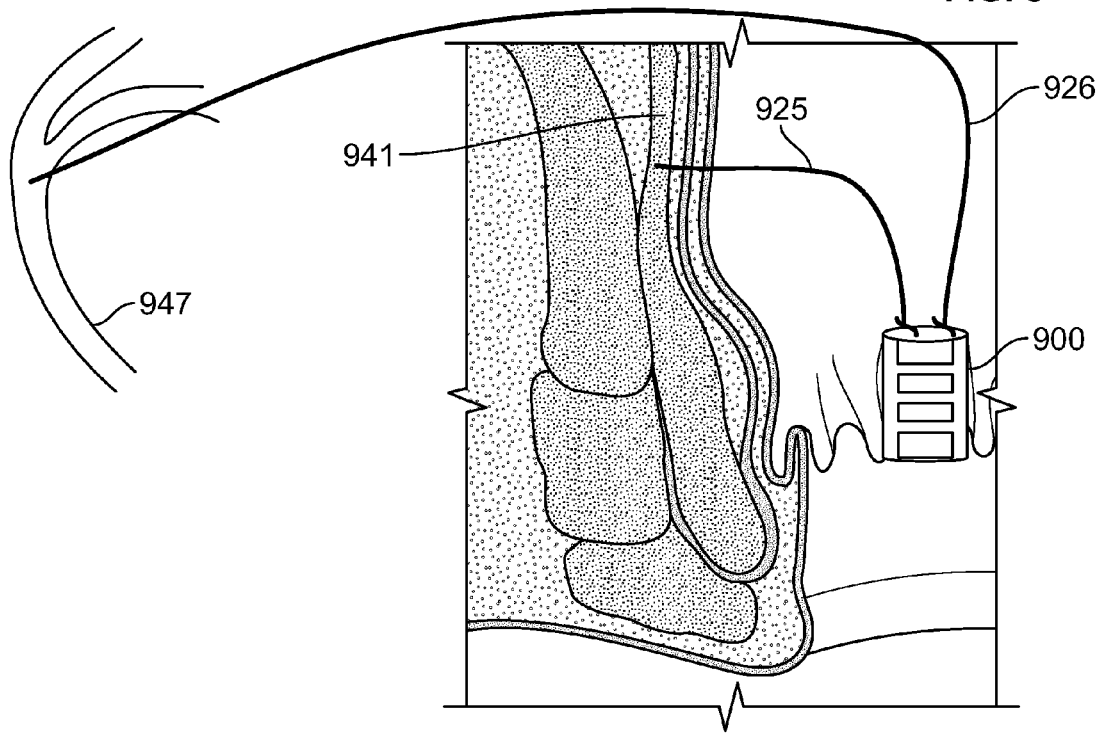
FIG. 9 is an illustration of one embodiment of an exemplary electrode set of a microdevice implanted in the circular muscle of the rectum and in a branch of the pudendal nerve.

FIG. 9 is an illustration of one embodiment of an exemplary electrode set 925, 926 of a microdevice 900 implanted in the circular muscle of the rectum 941 and in a branch of the pudendal nerve 947. The microdevice 900 is implanted such that a first electrode 925 is proximate the circular muscle layer of the rectum 941 while a second electrode 926 is proximate a branch of the pudendal nerve 947.

Figure 10:
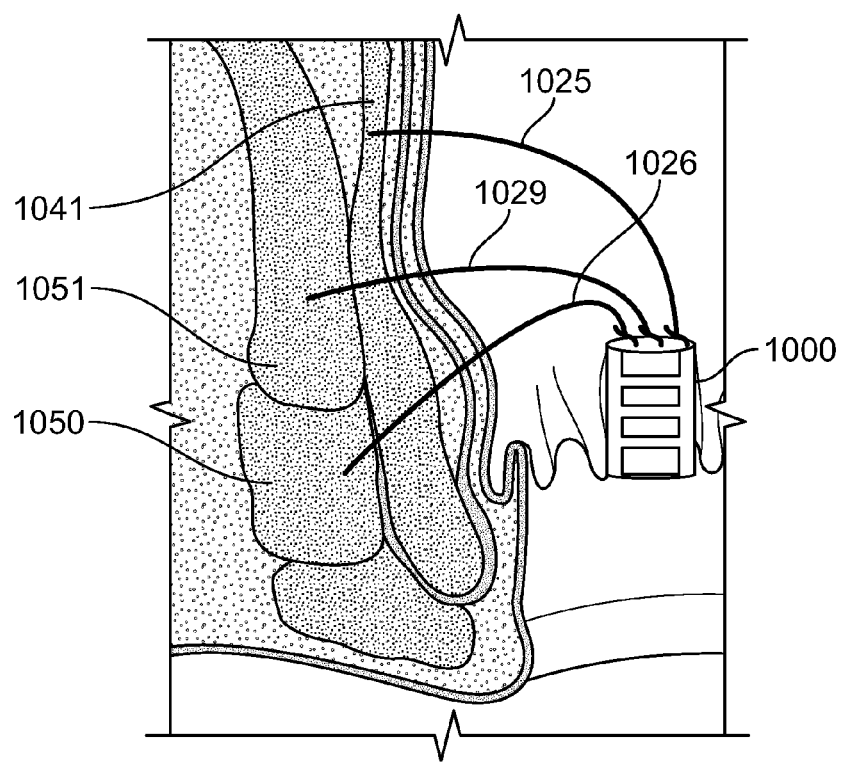
FIG. 10 is an illustration of one embodiment of an exemplary electrode set of a microdevice implanted in the circular muscle of the rectum and in the superficial and deep parts of the external anal sphincter.

FIG. 10 is an illustration of one embodiment of an exemplary electrode set 1025, 1026, 1029 of a microdevice 1000 implanted in the circular muscle of the rectum 1041 and in the superficial 1050 and deep 1051 parts of the external anal sphincter. The microdevice 1000 is implanted such that a first electrode 1025 is proximate the circular muscle layer of the rectum 1041 while a second electrode 1026 is proximate the superficial part of the external anal sphincter muscle 1050 and a third electrode 1029 is proximate the deep part of the external anal sphincter muscle 1051.

Figure 11:
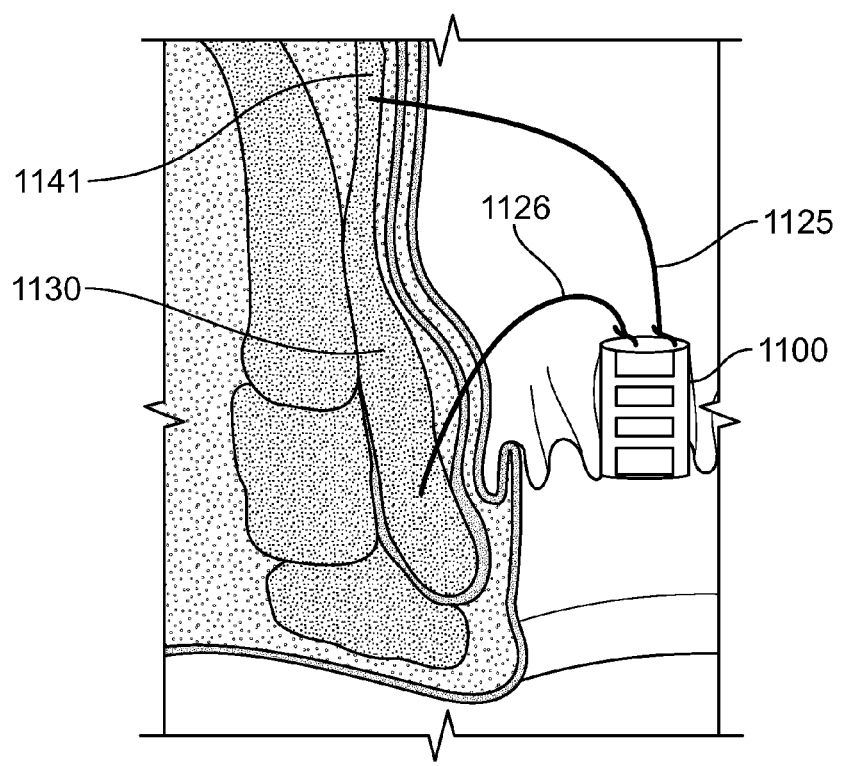
FIG. 11 is an illustration of one embodiment of an exemplary electrode set of a microdevice implanted in the circular muscle of the rectum and in the internal anal sphincter.

FIG. 11 is an illustration of one embodiment of an exemplary electrode set 1125, 1126 of a microdevice 1100 implanted in the circular muscle of the rectum 1141 and in the internal anal sphincter 1130. The microdevice 1100 is implanted such that a first electrode 1125 is proximate the circular muscle layer of the rectum 1141 and a second electrode 1126 is proximate the internal anal sphincter 1130.

To facilitate quick, easy and comfortable implantation of the microdevice, the present specification further provides an insertion device and catheter. FIGS. 12A through 12C depict various configurations of an embodiment of the insertion device 1200. FIG. 12A is an illustration of one embodiment of an exemplary insertion device 1200, depicting the step of pulling the plunger 1204 of the insertion device downward to create a vacuum and suck in a portion of anorectal tissue. FIG. 12B is a top-down view illustration of the same embodiment of an exemplary insertion device 1200 of FIG. 12A, depicting a portion of anorectal tissue 1206 sucked into the device. FIG. 12C is an illustration of the same embodiment of an exemplary insertion device 1200 of FIG. 12A, depicting the step of pushing the plunger 1204 of the insertion device 1200 upward to release the anorectal tissue.

In one embodiment, the insertion device 1200 comprises a generally conical portion 1201 that has a slot 1202 at a distance from a circular opening at the top that, in one embodiment, is covered with an optional movable valve 1203. A plunger 1204 slides through the lower cylindrical portion 1210 that also includes handle 1205. In one embodiment, a generally cylindrical channel is pre-formed within the insertion device 1200 through which a catheter is passed to implant the microdevice into the rectal mucosa and submucosa which has been sucked-in through the slot 1202. FIG. 12A specifically depicts the plunger 1204 being pulled downward to create a vacuum (with the valve 1203 closing) to suck anorectal tissue 1206 (seen in FIG. 12B), such as rectal mucosa and submucosa, into the slot 1202 of the insertion device 1200. FIG. 12B shows a top view of the insertion device 1200 with a requisite portion of the rectal mucosa and submucosa 1206 sucked into the slot 1202. A microdevice can then be inserted into the sucked-in tissue 1206 using a catheter as discussed later below. As shown in FIG. 12C, pushing the plunger 1204 upward opens the optional valve 1203, releasing the vacuum and also releasing the sucked-in tissue 1206 after the microdevice has been implanted therein.

In another embodiment, rather than using a plunger as described above, the vacuum is created by applying suction to the proximal end of the proximal portion of the insertion device. In one embodiment, a gauge is used to measure and standardize the amount of vacuum created.

FIGS. 13A through 13E depict various configurations of an embodiment of an implantation catheter 1300. The catheter 1300 is designed to pass through a pre-formed channel within the insertion device. FIG. 13A is an illustration of one embodiment of an exemplary configuration of an implantation catheter 1300 with a pusher 1312 and attached microdevice 1310 arranged predominantly parallel to each other within said catheter 1300. The catheter 1300 comprises an outer sheath 1311 to restrain a pusher 1312 and a microdevice 1310. At the pre-deployment stage of FIG. 13A, the pusher 1312 and microdevice 1310 are arranged to be predominantly parallel to each other and restrained within the sheath 1311. To facilitate this arrangement, a flexible portion 1320 of the leading end of the pusher 1312 is bent back inwards to form a sharp needle-like edge 1315. The microdevice 1310 is held at the tip of the inwardly bent portion 1320 of the pusher 1312.

FIG. 13B is an illustration of the same embodiment of an exemplary configuration of an implantation catheter 1300 in 13A, depicting the microdevice 1310 being pushed out of said catheter 1300 using the pusher 1312. During operation, as shown in FIG. 13B, the pusher 1312 begins to push the microdevice 1310 through the opening 1325 of the catheter deep into tissue. FIG. 13C is an illustration of the same embodiment of an exemplary configuration of an implantation catheter 1300 in 13A, depicting the microdevice 1310 fully pushed out of said catheter 1300. When the microdevice 1310 is fully pushed out of the sheath 1311, the bent portion 1320 springs outward (as a result of the recoil action due to the flexible bend) into a less acute angle, thereby separating the device 1310 from the sheath 1311. FIG. 13D is an illustration of the same embodiment of an exemplary configuration of an implantation catheter 1300 in 13A, depicting the pusher 1312 being pulled back into said catheter 1300. The pusher 1312 is pulled back into the sheath 1311, straightening the bent portion 1320 and consequently nudging the device 1310 deeper into the tissue. FIG. 13E is an illustration of the same embodiment of an exemplary configuration of an implantation catheter 1300 in 13A, depicting the pusher 1312 pulled back completely into said catheter 1300. Pulling the pusher 1312 completely into the sheath 1311 disconnects the device 1310 from the pusher 1312, thus releasing the device 1310 in the tissue site.

Figure 14A:
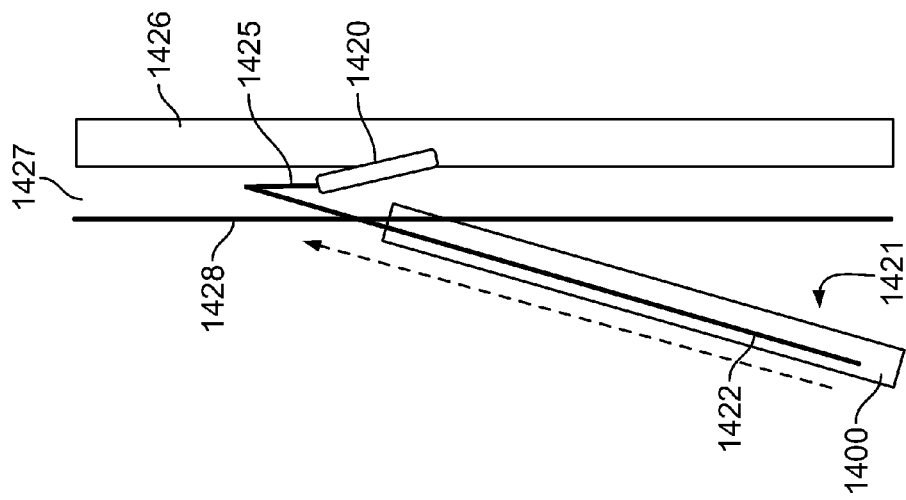
FIG. 14A is an illustration of one embodiment of an exemplary configuration of an implantation catheter, depicting said catheter positioned near the intestinal mucosa of a patient.
Figure 14B:
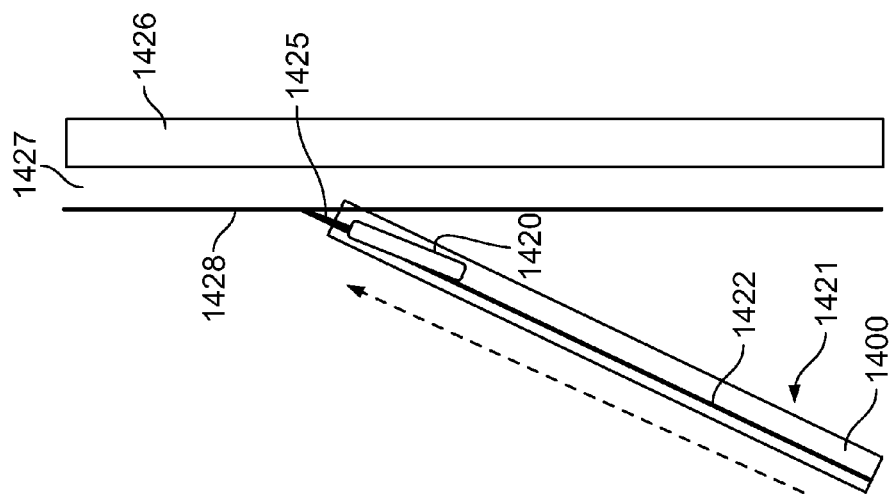
FIG. 14B is an illustration of the same embodiment of an exemplary configuration of an implantation catheter of FIG. 14A, depicting the step of a microdevice being pushed out of the catheter for implantation.
Figure 14C:
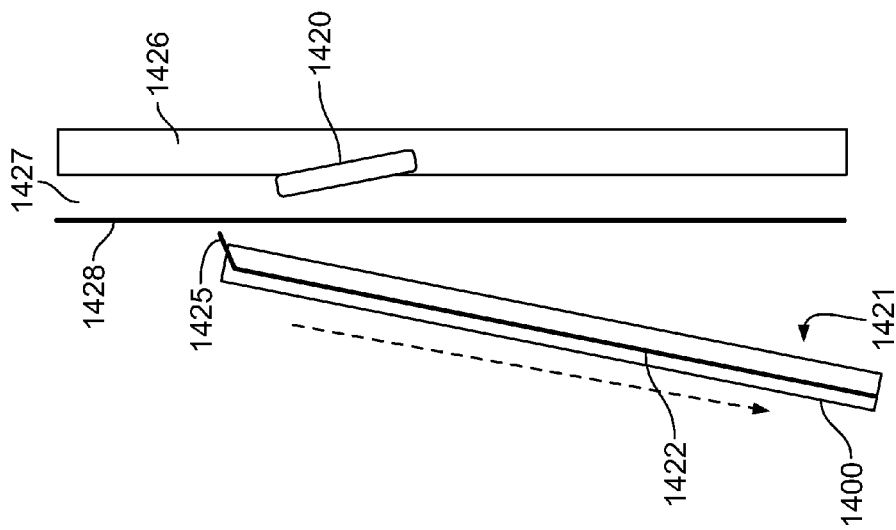
FIG. 14C is an illustration of the same embodiment of an exemplary configuration of an implantation catheter of FIG. 14A, depicting the step of the microdevice being deployed deeper into the tissue site due to straightening of the bent portion.
Figure 14D:
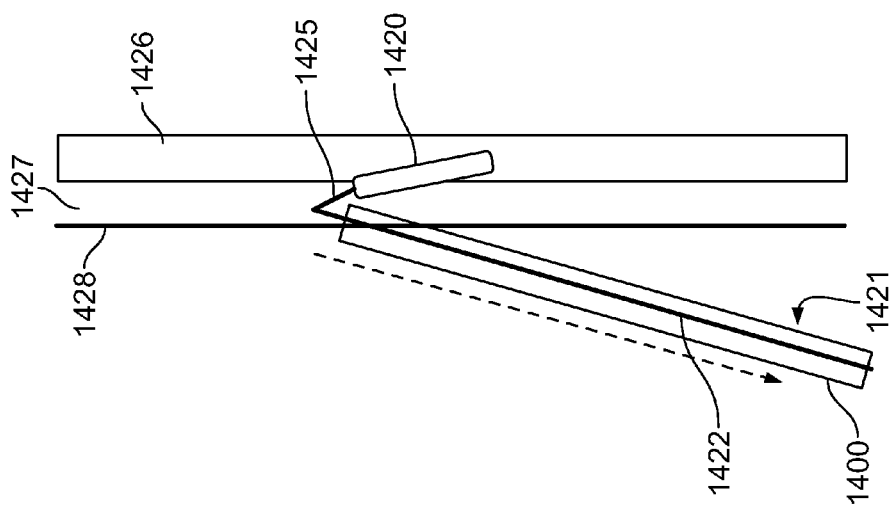
FIG. 14D is an illustration of the same embodiment of an exemplary configuration of an implantation catheter of FIG. 14A, depicting the step of the catheter being pulled away after releasing the microdevice at the tissue site.

FIGS. 14A through 14D are illustrations of the steps used for implantation of the microdevice 1420 into tissue such as mucosa 1428, submucosa 1427, and muscularis propria 1426. FIG. 14A is an illustration of one embodiment of an exemplary configuration of an implantation catheter 1400, depicting said catheter 1400 positioned near the intestinal mucosa 1428 of a patient. The catheter sheath 1421 is positioned near the mucosa 1428 of a patient. The pusher 1422 and microdevice 1420 are positioned within the sheath 1421. FIG. 14B is an illustration of the same embodiment of an exemplary configuration of an implantation catheter 1400 in 14A, depicting the step of a microdevice 1420 being pushed out of the catheter 1400 for implantation. The microdevice 1420 is pushed out of the sheath 1421 using the pusher 1422, causing the sharp edge created at the bent portion 1425 to pierce the tissue and implant the microdevice 1420. The microdevice 1420 is implanted such that one end of the microdevice 1420 is proximate the submucosa 1427 and the opposite end is proximate the muscularis propria 1426. FIG. 14C is an illustration of the same embodiment of an exemplary configuration of an implantation catheter 1400 in 14A, depicting the step of the microdevice 1420 being deployed deeper into the tissue site due to straightening of the bent portion 1425. The pusher 1422 is slowly pulled back, straightening the bent portion 1425 and deploying the device 1420 deeper into the tissue. FIG. 14D is an illustration of the same embodiment of an exemplary configuration of an implantation catheter 1400 in 14A, depicting the step of the catheter 1400 being pulled away after releasing the microdevice 1420 at the tissue site. The microdevice 1420 is released at the tissue site and the sheath 1421 is pulled away. In this embodiment, the tip can be shaped or designed with a cutting edge to facilitate insertion. Additionally, in one embodiment, injection of cushioning material such as saline is used to create a larger submucosal pocket to accommodate a larger device.

Figure 15:
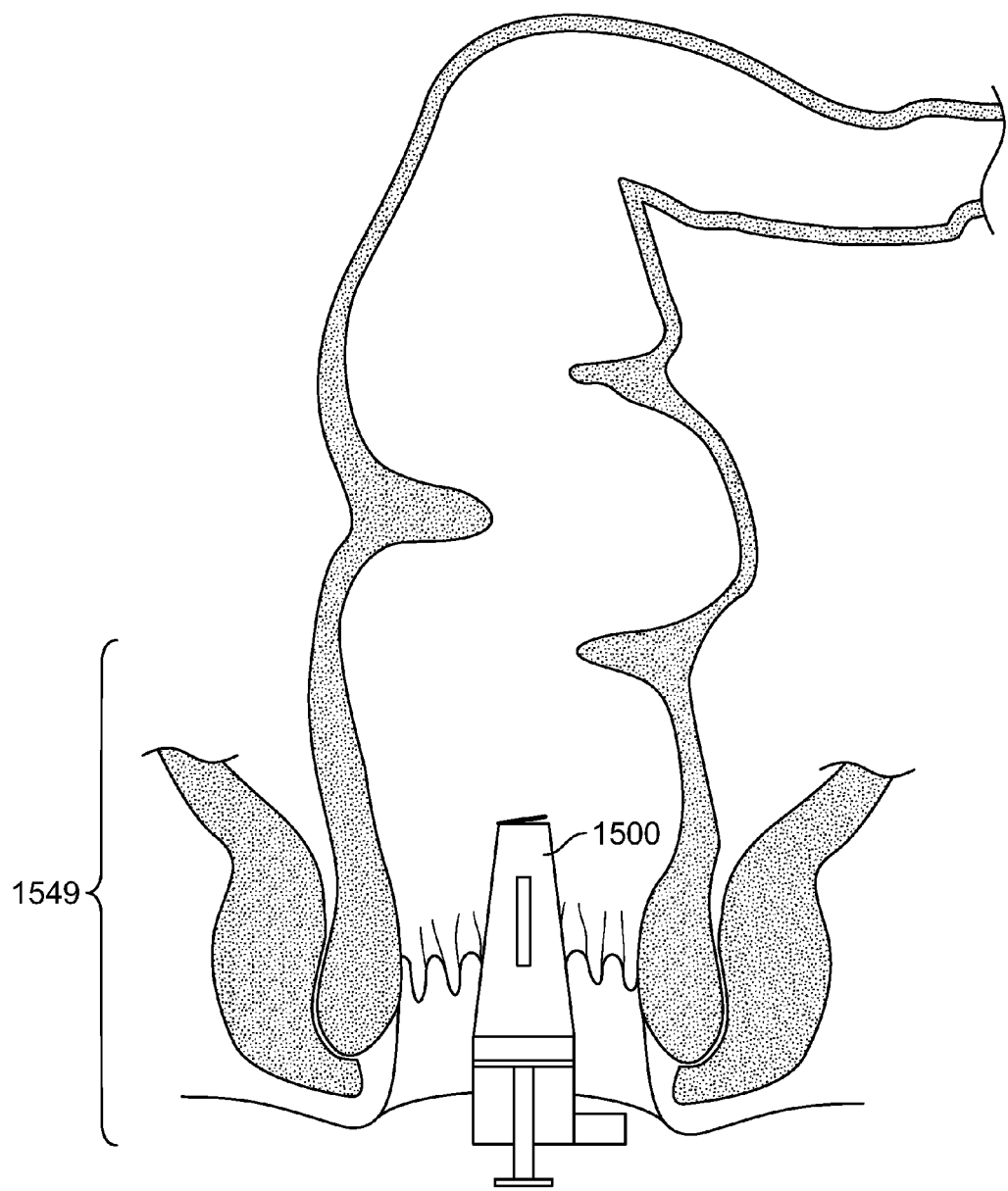
FIG. 15 is an illustration of one embodiment of an exemplary insertion device placed in the anorectal region of a patient for microdevice delivery.
Figure 16:
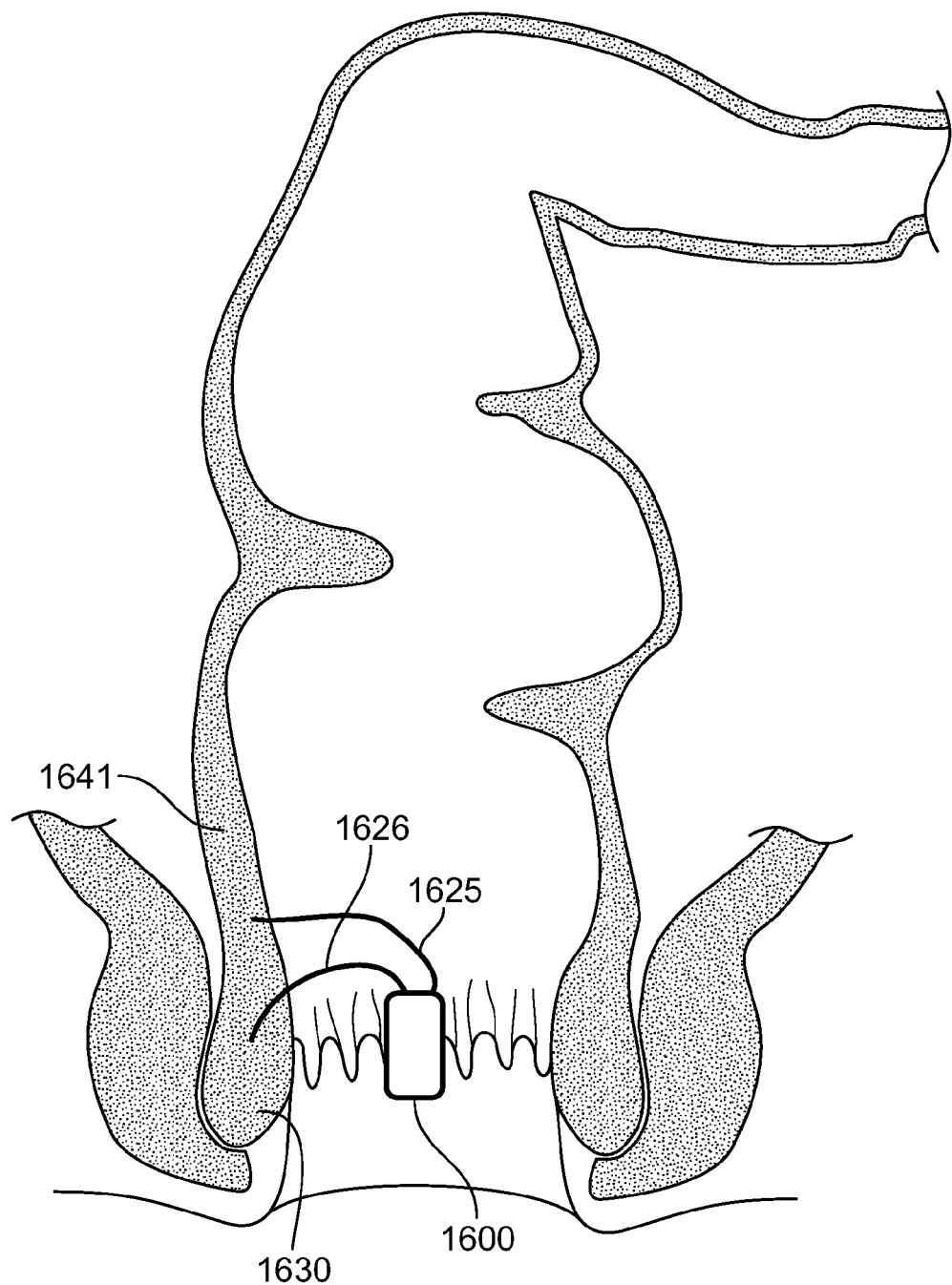
FIG. 16 is an illustration of one embodiment of a microdevice, with attached electrode set, implanted in the anorectal submucosa.

FIG. 15 is an illustration of one embodiment of an exemplary insertion device 1500 placed in the anorectal region 1549 of a patient for microdevice delivery. The insertion device 1500 is placed in the anorectal region 1549 of a patient for localization of appropriate site(s) and sucking-in tissue (as discussed with reference to FIGS. 12A through 12C). FIG. 16 is an illustration of one embodiment of a microdevice 1600 with attached electrode set 1625, 1626 implanted in the anorectal submucosa. The microdevice 1600 is implanted with a first electrode 1625 placed proximate the rectal circular muscle layer 1641 and a second electrode 1626 placed proximate the internal anal sphincter 1630.

Figure 17:
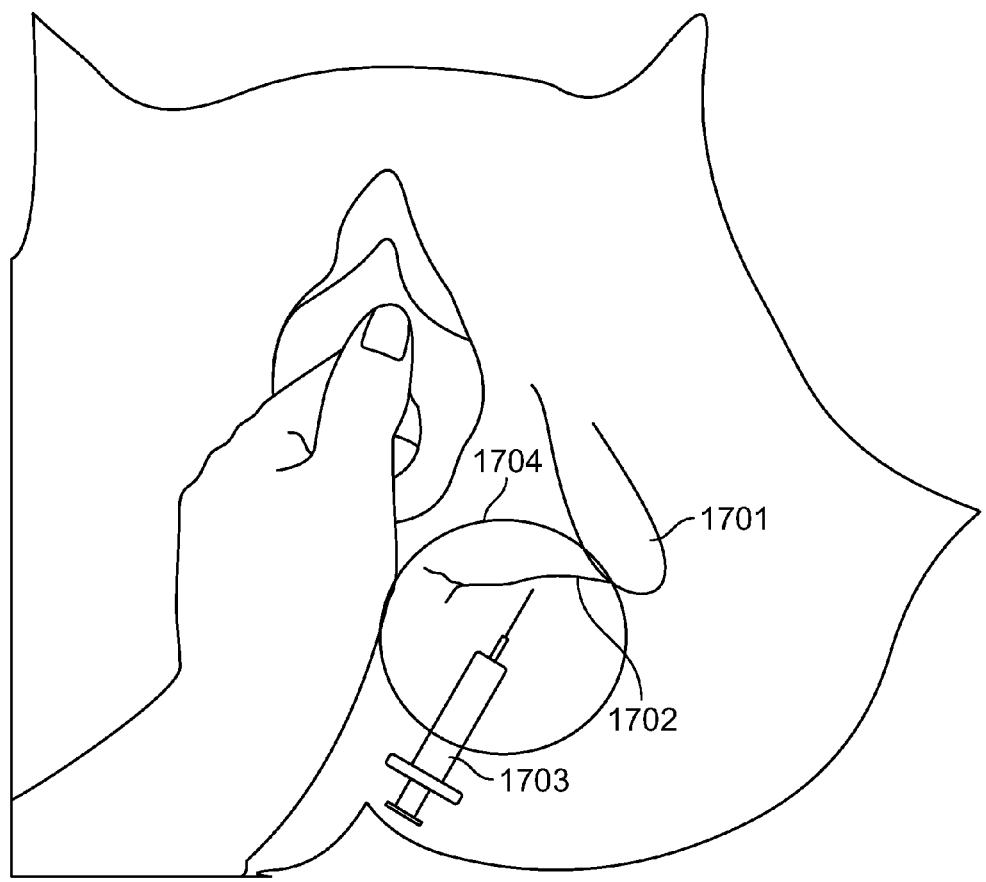
FIG. 17 is an illustration of one embodiment of the present specification depicting a method of implanting a microdevice in a female patient using a hypodermic needle.

FIG. 17 is an illustration of one embodiment of the present specification depicting a method of implanting a microdevice in a female patient using a hypodermic needle 1703. The ischial tuberosity 1701 is identified by pervaginal palpation and the microdevice is implanted percutaneously using the hypodermic needle 1703, proximate a pudendal nerve 1702. The circle 1704 depicts the preferred area for implantation of the microdevice in accordance with this embodiment.

In another embodiment, the microdevice is implanted perrectally to have one electrode of the device proximate a pudendal nerve and the second electrode proximate an anorectal structure. The perrectal or pervaginal implant method could be further assisted by imaging techniques, such as, ultrasound.

Figure 18:
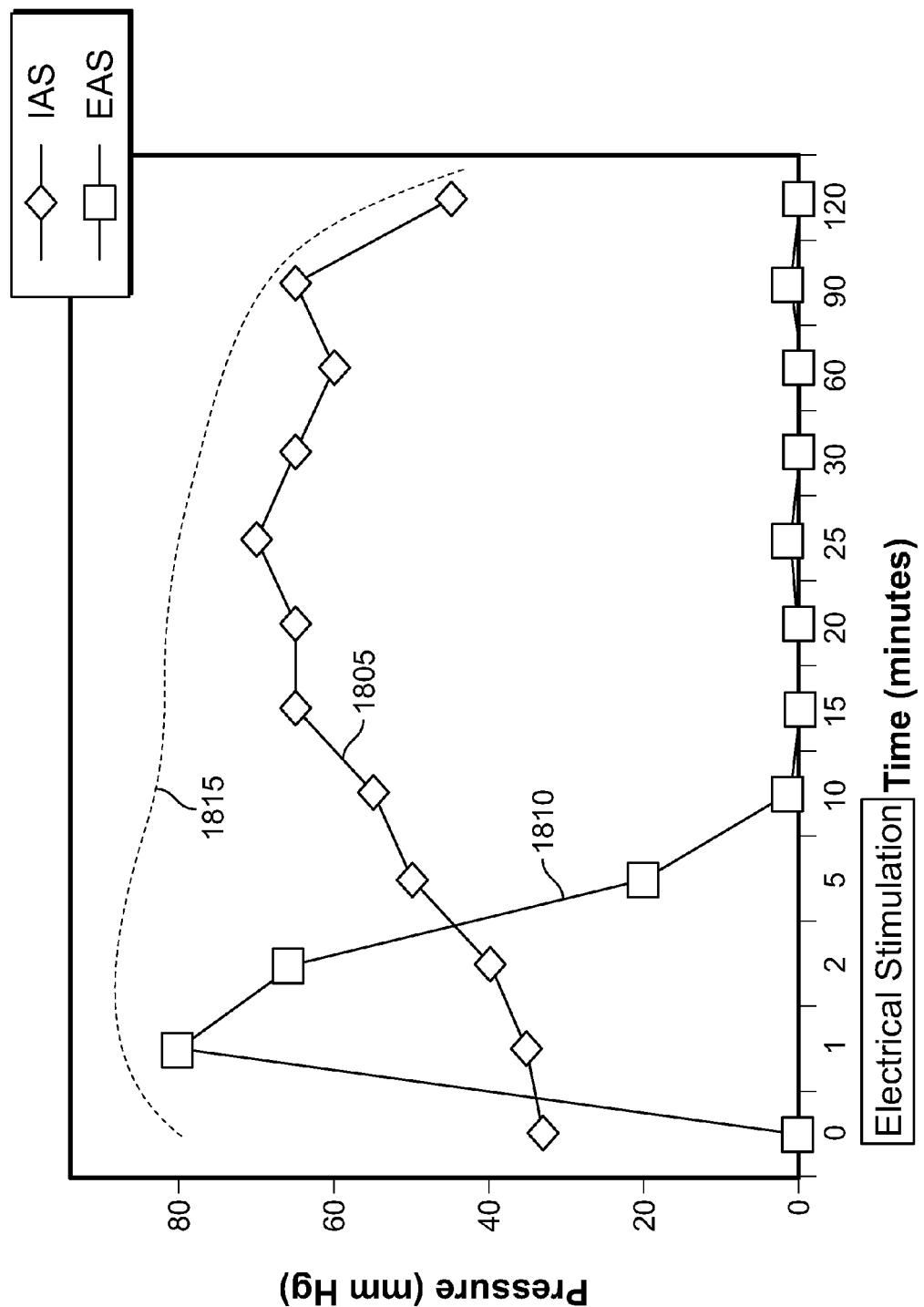
FIG. 18 is a graph depicting representative pressure curves obtained by exemplary selective stimulation of the internal anal sphincter (IAS) and external anal sphincter (EAS), in accordance with one embodiment of the present specification.

FIG. 18 is a graph depicting representative pressure curves 1805, 1810, 1815 obtained by exemplary selective stimulation of the internal anal sphincter (IAS) and external anal sphincter (EAS), in accordance with one embodiment of the present specification. Pressure curve 1805 was obtained by selective stimulation of the IAS only. The rise in IAS pressure is non-instantaneous and the improved IES pressure exceeds the duration of electrical stimulation. In one embodiment, the LES pressure remains at the improved level for at least five minutes after the cessation of electrical stimulation. Pressure curve 1810 was obtained by selective stimulation of the EAS only. The rise in EAS pressure is instantaneous and the improved IES pressure subsides after a few minutes despite continued electrical stimulation. Pressure curve 1815 represents the cumulative pressure curve obtained by simultaneous stimulation of the IAS and EAS. The rise in the composite sphincter pressure is instantaneous and attributable predominantly to the contribution made by the EAS pressure and, is sustained beyond the duration of stimulation and is attributable predominantly to the contribution made by the IAS pressure.

In one embodiment, wherein electrical stimulation is adapted to modulate the function of an internal anal sphincter according to the present specification, such modulation of the internal anal sphincter function is further modulated by rectal distension. In one embodiment, the additional modulation of the internal anal sphincter function by rectal distension results in an increase or a decrease by at least 10% of the initial modulation of said function due to the stimulation.

Figure 19C:
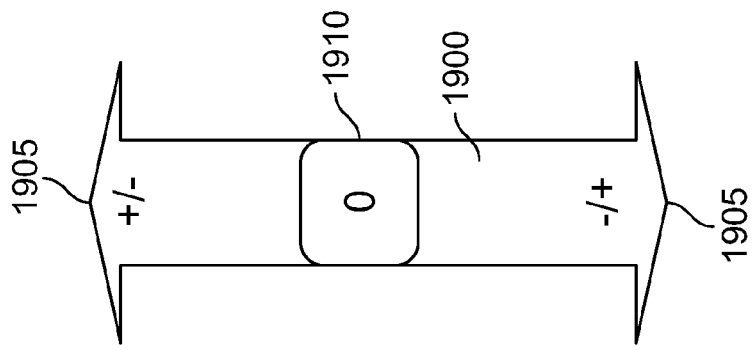
FIG. 19A is an illustration of one embodiment of a microdevice with end electrodes comprising anodes and the center electrode comprising a cathode.
FIG. 19B is an illustration of one embodiment of a microdevice with end electrodes comprising cathodes and the center electrode comprising an anode; and, FIG. 19C is an illustration of one embodiment of a microdevice with end electrodes comprising an anode and a cathode and the center electrode comprising no polarity.
Figure 19B:
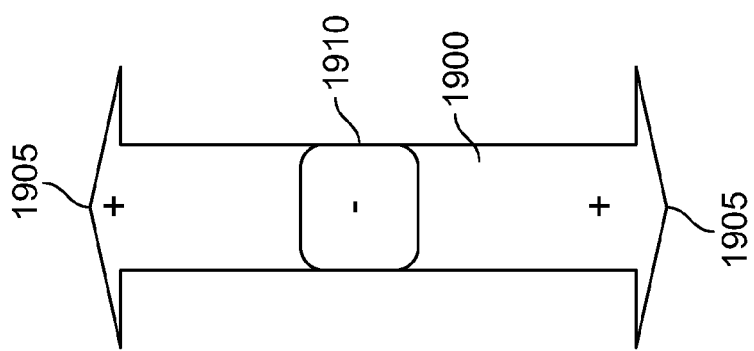
Figure 19A:
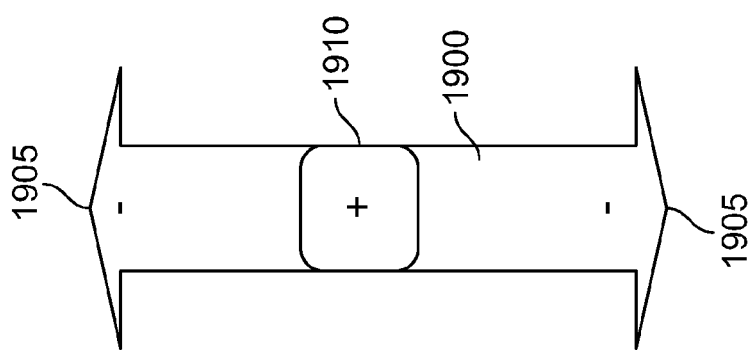

FIGS. 19A through 19C depict further embodiments of the microdevice. FIG. 19A is an illustration of one embodiment of the microdevice 1900 with end electrodes 1905 as anodes and center electrode 1910 as cathode. FIG. 19B is an illustration of another embodiment of the microdevice 1900 with end electrodes 1905 as cathodes and center electrode 1910 as anode. FIG. 19C is an illustration of yet another embodiment of the microdevice 1900 with end electrodes 1905 as anode and cathode and center electrode 1910 with no polarity. The microdevice 1900 comprises three electrodes such that each pair of electrodes can be individually controlled to stimulate different anatomical structures using the same or different stimulation algorithms.

In one embodiment, a single microdevice is implanted into two contiguous anatomical structures (such as two proximate nerves or two proximate muscles or into a proximate nerve and muscle structure) with one electrode each in the two contiguous structures. Thereafter, the two contiguous structures are selectively stimulated, simultaneously or at separate times, by using the structure specific electrode, stimulation pulse patterns, waveforms, or algorithms. For example, the microdevice can be implanted proximate to a nerve and a muscle and a long-pulse (1 msec-1 sec) is used to stimulate the muscle structure while a short pulse (10 uSec-999 msec) is used to stimulate the nerve structure, thus getting the benefits of both nerve and muscle stimulation from one microdevice implant. In another embodiment, the electrode proximate the desired structure is used as a depolarizing electrode and the electrode proximate the other structure is used as the hyperpolarizing electrode to selectively stimulate the first structure.

In another embodiment the microdevice is implanted proximate a nerve structure comprising both afferent sensory and efferent motor nerves. At different times, based on patient input or a physiological sensory input, the single microdevice can stimulate the motor nerves using a low frequency (<100 Hz) and inhibit the sensory nerves using a high frequency (>100 Hz) or vice-versa, depending on the desired physiological outcome. This will result in increasing the tone of the sphincter muscle while simultaneously blocking an urge sensation from the rectum.

In another embodiment, the microdevice is implanted with one electrode each in a submucosal space and a muscle structure. The submucosal nerves are stimulated using a short pulse (<1 msec) and the muscle using a long pulse (≥1 msec). Alternating between submucosal nerve stimulation and direct muscle stimulation eliminates the problem of tolerance or fatigue by continuous stimulation of only nerve or only muscle.

In one example, the microdevice is implanted with each end electrode in an internal and an external anal sphincter wherein the internal anal sphincter is stimulated using a more continuous stimulation pulse pattern or algorithm to maintain a continuous basal tone to prevent anal seepage while the external anal sphincter is stimulated more on-demand to prevent untimely defecation. In addition, the internal anal sphincter is stimulated with a short-pulse to stimulate the nerves in or proximate the internal anal sphincter and the external anal sphincter is stimulated with a long-pulse to achieve direct muscle stimulation or vice-versa. The frequency of the pulse can also be varied to differentially stimulate nerves or muscles or to block the sensation being transmitted through a nerve.

In another embodiment of the present specification, the microdevice is implanted in the rectal submucosa with one electrode proximate the submucosal nerve plexus and the other electrode proximate the myenteric nerve plexus. The myenteric nerve plexus is stimulated with a low frequency pulse pattern or algorithm to stimulate the myenteric nerves whereas the submucosal plexus is stimulated with a high-frequency pulse pattern or algorithm to block the submucosal plexus or vice-versa. In another embodiment the two plexuses are stimulated with the same pattern or algorithm of pulses at different times to achieve a desired physiological effect.

In another embodiment, the microdevice is implanted in the anorectal wall with one electrode proximate the anorectal nerve plexus and the other electrode proximate a branch of the pudendal nerve or the sacral nerve. The anorectal nerve plexuses are stimulated in a more continuous fashion to maintain basal internal anal sphincter tone while the pudendal or the sacral nerves are stimulated in a more on demand fashion to generate external anal sphincter squeeze pressures to abort or prevent untimely defecation.

In another embodiment, the microdevice is implanted along the length of the pudendal or sacral nerve where the proximate pair of electrodes delivers a high-frequency blocking pulse to block the sensory afferent sensation to the brain and the distal pair of the electrode delivers a low-frequency stimulating pulse to stimulate one or both of the internal and external anal sphincters to maintain basal resting tone and/or generate squeeze pressures.

In another embodiment, the microdevice is implanted along the length of the pudendal or sacral nerve where the proximate pair of electrodes delivers a low-frequency stimulating pulse to stimulate the sensory afferent sensation to the brain and the distal pair of the electrode delivers a high-frequency blocking pulse to block one or both of the internal and external anal sphincters to eliminate the basal resting tone and/or eliminate the squeeze pressures thus initiating a bowel movement in a patient with defecatory disorders such as constipation.

In another embodiment, the microdevice is implanted with each end electrode in a deep part and a superficial part of the external anal sphincter wherein the two parts of the external anal sphincter are stimulated alternately, allowing one part to rest while the other is stimulated, hence increasing the duration of the squeeze pressure without the problem of tolerance or muscle fatigue. In addition, the two parts of the external anal sphincter can be stimulated alternately with a short-pulse to stimulate the nerves in or proximate the external anal sphincter and with a long-pulse to achieve direct external anal muscle stimulation, hence further increasing the duration of the squeeze pressure without the problem of tolerance or muscle fatigue.

In another embodiment, the microdevice is implanted with an electrode each in the inner circular muscle layer of the distal rectum and the internal anal sphincter wherein the two structures are simultaneously stimulated. This configuration allows both physiological structures to contract synchronously and synergistically increasing the length of the high pressure zone at the rectal outlet effectively increasing the functional length of the anal sphincter. This results in an increased effective competence of the sphincter even at the lower range of sphincter pressure. This embodiment allows maintaining sphincter competence even at low levels of electrical stimulation and hence decreasing the problem of tolerance or muscle fatigue which is usually observed at higher levels of electrical stimulation. In addition, the circular muscle of the rectum is enabled to work as a high pressure zone and a functional sphincter, thus maintaining continence in patients with a damaged sphincter such as those of women with traumatic delivery resulting in perineal tear and anal sphincter damage.

In another embodiment, the microdevice is implanted with an electrode each in the inner circular muscle layer of the distal rectum and the internal anal sphincter wherein the two structures are sequentially stimulated. This allows for the rectum to contract and the anal canal to relax resulting in defecation. This configuration enables treatment of outlet type constipation due to dyssynergic sphincter dysfunction.

Patients with irritable bowel syndrome commonly suffer from alternating constipation and diarrhea with symptoms of fecal urgency. In one embodiment, the electro-medical device of the present specification allows the patient to control the respective symptoms using different electrode combinations and different stimulation algorithms, as described above.

In another embodiment, the device of the present specification can be embodied using a standard implantable pulse generator implanted surgically into a patient's body and the electrodes implanted proximate to the target tissue, using standard lead implantation techniques.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A method of treating anorectal dysfunction in a patient, comprising the following steps:
Implanting a device comprising at least a first electrode and a second electrode operably connected to an electrical stimulus generator in anorectal tissue of the patient, wherein said anorectal tissue comprises an internal anal sphincter and an external anal sphincter;
Causing said stimulus generator to deliver a first electrical pulse via said first electrode to the internal anal sphincter to cause a stimulation of said internal anal sphincter and a modulation of an internal anal sphincter pressure; and
Causing said stimulus generator to deliver a second electrical pulse via said second electrode to the external anal sphincter to cause a stimulation of said external anal sphincter and a modulation of an external anal sphincter pressure, wherein the delivery of said first electrical pulse and said second electrical pulse substantially instantaneously modulates a composite anal sphincter pressure.

2. The method of claim 1 wherein the first electrode physically contacts the internal anal sphincter and wherein the second electrode physically contacts the external anal sphincter.

3. The method of treating anorectal dysfunction of claim 1, wherein said stimulus generator is capable of generating pulse trains and wherein at least one of the following parameters is programmable: numbers of pulses per pulse train, intervals between pulse trains, durations of each pulse, timings and amplitudes of pulses in a pulse train, desired amounts of amperage or potential in a pulse, or shapes of pulses in pulse trains, wherein the shape is chosen from any one of the following: a square, rectangular, sinusoidal, or saw tooth shape.

4. The method of treating anorectal dysfunction of claim 1, wherein said stimulus generator generates the first electrical pulse pursuant to a first stimulation algorithm and said stimulus generator generates the second electrical pulse pursuant to a second stimulation algorithm.

5. The method of treating anorectal dysfunction of claim 1, wherein said first electrode functions as a depolarizing electrode and said second electrode functions as a hyperpolarizing electrode.

6. The method of treating anorectal dysfunction of claim 5, wherein said depolarizing electrode is positioned proximate the patient's internal anal sphincter for stimulation of said internal anal sphincter.

7. The method of treating anorectal dysfunction of claim 5, wherein said depolarizing electrode is positioned proximate the patient's external anal sphincter for stimulation of said external anal sphincter.

8. The method of treating anorectal dysfunction of claim 4, wherein said first stimulation algorithm is different than said second stimulation algorithm.

9. The method of treating anorectal dysfunction of claim 8, wherein said first stimulation algorithm is configured to modulate a function of the patient's internal anal sphincter and said second stimulation algorithm is configured to modulate a function of the patient's external anal sphincter.

10. The method of treating anorectal dysfunction of claim 8, wherein said first stimulation algorithm causes the first electrical pulse to be delivered continuously or at regular intervals and said second stimulation algorithm causes the second electrical pulse to be delivered at irregular intervals or on demand.

11. The method of treating anorectal dysfunction of claim 8, wherein said first stimulation algorithm is programmed into the device such that the first electrical pulse is delivered without patient intervention and said second electrical pulse is manually delivered by the patient via an external input.

12. The method of treating anorectal dysfunction of claim 11, wherein said first stimulation algorithm is programmed based on patient's clinical symptoms or rectal manometry data and stored in a memory in said device.

13. The method of treating anorectal dysfunction of claim 4, wherein said device further comprises at least one sensor, wherein said sensor detects at least one parameter, and wherein data obtained by said sensor is used to modify said first stimulation algorithm and/or said second stimulation algorithm.

14. The method of treating anorectal dysfunction of claim 13, wherein said sensor comprises at least one of a pressure sensor, an electrical activity sensor, an impedance sensor, an accelerometer, or an inclinometer.

15. The method of treating anorectal dysfunction of claim 13, wherein said sensor comprises an internal pressure sensor configured such that, when the patient initiates an anal squeeze, said squeeze is sensed by said internal pressure sensor and causes said device to deliver an electrical pulse to the patient's external anal sphincter to raise the external anal sphincter tone.

16. The method of treating anorectal dysfunction of claim 4, wherein said device further comprises an external controller configured to be operated by said patient and wherein the external controller is adapted to modify or activate at least one of said first stimulation algorithm or said second stimulation algorithm.

17. A method of modulating a function of an internal anal sphincter in a patient, comprising the following steps:
Implanting a stimulus generator, wherein said stimulus generator is operably connected to a first electrode and a second electrode;
Implanting said first electrode within an internal anal sphincter of the patient's anorectal region;
Implanting said second electrode within an external anal sphinctera of the patient's anorectal region;
Causing said stimulus generator to generate a first stimulation, wherein said first stimulation is adapted to modulate a function of the internal anal sphincter; and
Causing said stimulus generator to generate a second stimulation, wherein said second stimulation is adapted to modulate a function of the external anal sphincter, wherein the delivery of said first stimulation and said second stimulation substantially instantaneously modulates a composite anal sphincter function.

18. The method of modulating the function of the internal anal sphincter in the patient of claim 17 wherein said modulation is adapted to last beyond a cessation of such stimulation.

19. The method of modulating the function of the internal anal sphincter in the patient Of claim 18, wherein the modulation lasts for at least 5 minutes after the cessation of the stimulation.

20. The method of modulating the function of the internal anal sphincter in the patient of claim 17, wherein said modulation of the internal anal sphincter function is further modulated by rectal distension.

21. The method of modulating the function of the internal anal sphincter in the patient of claim 20, wherein the additional modulation of the internal anal sphincter function by rectal distension results in an increase or a decrease by at least 10% of the modulation of said function due to the stimulation.

* * * * *